United States Patent [19]

Fryer et al.

[11] Patent Number: 4,481,142
[45] Date of Patent: Nov. 6, 1984

[54] PYRIMIDO-2-BENZAZEPINES

[75] Inventors: Rodney I. Fryer, North Caldwell; Norman W. Gilman, Wayne; Eugene J. Trybulski, Parsippany; Armin Walser, West Caldwell, all of N.J.

[73] Assignee: Hoffmann-La Roche Inc., Nutley, N.J.

[21] Appl. No.: 437,047

[22] Filed: Oct. 27, 1982

Related U.S. Application Data

[63] Continuation of Ser. No. 151,025, May 19, 1980, abandoned, which is a continuation-in-part of Ser. No. 16,709, Mar. 1, 1979, abandoned.

[51] Int. Cl.³ .......................................... C07D 487/04
[52] U.S. Cl. ................................. 260/243.3; 544/335; 549/445
[58] Field of Search ...................................... 260/243.3

[56] References Cited

U.S. PATENT DOCUMENTS 3,599,300  5/1976  Finizio ............................. 424/263

FOREIGN PATENT DOCUMENTS 833249  9/1975  Belgium .

Primary Examiner—Glennon H. Hollrah
Assistant Examiner—D. B. Springer
Attorney, Agent, or Firm—Jon S. Saxe; Bernard S. Leon; Frank P. Hoffman

[57] ABSTRACT

There is presented compounds of the formula

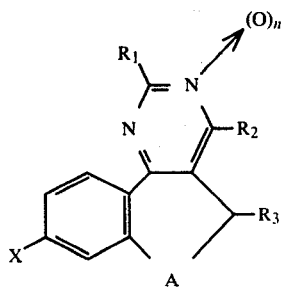

wherein A is selected from the group consisting of

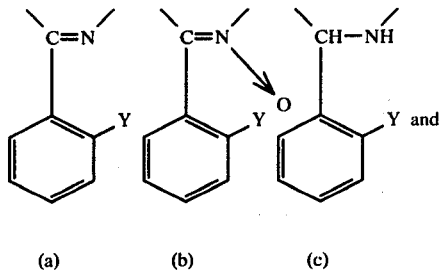

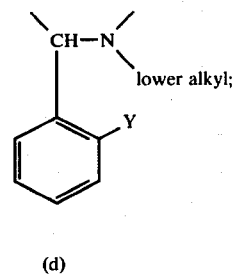

$R_1$ is selected from the group consisting of hydrogen, chlorine, bromine, lower alkyl, the group $NR_4R_5$, the group $-CH_2-CO-R_7$, the group $-NH(CH_2)_mNR_8R_9$, hydroxy, lower alkoxy, mercapto and lower alkyl mercapto; $R_2$ is selected from the group consisting of hydrogen, amino and dilower alkyl amino; $R_3$ is selected from the group consisting of hydrogen, lower acyloxy and hydroxy; X is selected from the group consisting of hydrogen, halogen, trifluoromethyl, ethyl, α-hydroxy ethyl and acetyl; Y is hydrogen or halogen; $R_4$ and $R_5$ are hydrogen or lower alkyl or together with their co-bonded nitrogen atom form a five to seven membered heterocyclic group; $R_7$ is selected from the group consisting of hydroxy lower alkoxy and $NR_8R_9$; $R_8$ and $R_9$ are hydrogen or lower alkyl; n is 0 or 1 and m is 1 to 7 with the limitations that (1) at least one of $R_1$ and $R_2$ are hydrogen, (2) when $R_3$ is lower acyloxy or hydroxy, A is the group (a), X is hydrogen, halogen, trifluoromethyl, ethyl or acetyl and $R_1$ is the group $-NH(CH_2)_mNR_8R_9$, then $R_8$ and $R_9$ are lower alkyl, (3) when A is group (d) and $R_1$ is the group $-NH(CH_2)_mNR_8R_9$ then $R_8$ and $R_9$ are lower alkyl and (4) when n is 1, $R_1$ is hydrogen, lower alkyl, lower alkoxy, chlorine, bromine or the group $-CH_2-CO-R_7$ with $R_7$ as above then A is the group (a) or (b) and the pharmaceutically acceptable salts thereof.

The compounds exhibit pharmacological activity as anxiolytics and sedatives.

Also presented Are various novel intermediates and processes to produce the above end products.

13 Claims, No Drawings

PYRIMIDO-2-BENZAZEPINES

RELATED APPLICATIONS

This is a continuation, of application Ser. No. 151,025 filed May 19, 1980 (abandoned), which is a continuation-in-part of Ser. No. 16,709, filed Mar. 1, 1979 (abandoned).

DESCRIPTION OF THE INVENTION

The present invention relates to compounds of the formula

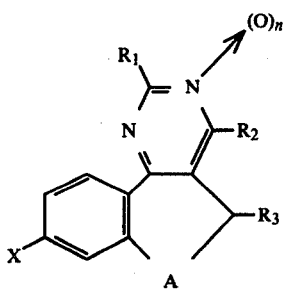

wherein A is selected from the group consisting of

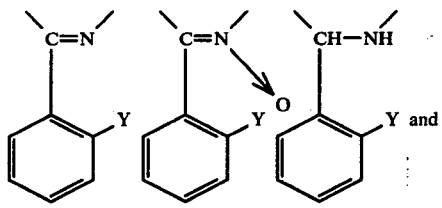

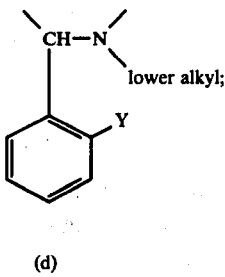

$R_1$ is selected from the group consisting of hydrogen, chlorine, bromine, lower alkyl, the group $NR_4R_5$, the group —$CH_2$—CO—$R_7$, the group —$NH(CH_2)_mNR_8R_9$, hydroxy, lower alkoxy, mercapto and lower alkyl mercapto; $R_2$ is selected from the group consisting of hydrogen, amino and di-lower alkyl amino; $R_3$ is selected from the group consisting of hydrogen, lower acyloxy and hydroxy; X is selected from the group consisting of hydrogen, halogen, trifluoromethyl, ethyl, α-hydroxy ethyl and acetyl; Y is hydrogen or halogen; $R_4$ and $R_5$ are hydrogen or lower alkyl or together with their co-bonded nitrogen atom form a five to seven membered heterocyclic group; $R_7$ is selected from the group consisting of hydroxy lower alkoxy and $NR_8R_9$; $R_8$ and $R_9$ are hydrogen or lower alkyl; n is 0 or 1 and m is 1 to 7 with the limitation that (1) at least one of $R_1$ and $R_2$ are hydrogen, (2) when $R_3$ is lower acyloxy or hydroxy, A is the group (a), X is hydrogen, halogen, trifluoromethyl, ethyl or acetyl and $R_1$ is the group —$NH(CH_2)_mNR_8R_9$, then $R_8$ and $R_9$ are lower alkyl, (3) when A is group (d) and $R_1$ is the group —$NH(CH_2)_mNR_8R_9$ then $R_8$ and $R_9$ are lower alkyl and (4) when n is 1, $R_1$ is hydrogen, lower alkyl, lower alkoxy, chlorine, bromine or the group —$CH_2$—CO—$R_7$ with $R_7$ as above then A is the group (a) or (b) and the pharmaceutically acceptable salts thereof.

The compounds exhibit pharmacological activity an anxiolytics and sedatives.

As used herein, the term "lower alkyl" means straight or branched hydrocarbon groups having from 1 to 7 carbon atoms, preferably 1 to 4 carbon atoms such as methyl, ethyl, propyl, isopropyl and the like.

The term "halogen" represents all four forms thereof, i.e., fluorine, chlorine, iodine and bromine unless expressly indicated otherwise.

The terms "lower alkoxy" and "lower alkyl mercapto" denote a moiety of the formula —O-lower alkyl and —S-lower alkyl, respectively, wherein lower alkyl is as above.

Where the term "heteroatom" or "carbon atom nucleophiles" is utilized there are meant moieties as described in Belgian Pat. No 833,249 which disclosure is incorporated by reference herein.

Where the moiety $NR_4R_5$ represents a five to seven member heterocyclic group, it may also contain an oxygen or sulfur atom or the group >N-lower alkyl. Representative groups include morpholine, piperidine, 3-pyrroline, piperazine, azetidine, aziridine, pyrrolidine and hexamethyleneimine.

By the term "acyl" alone or in "acyloxy" is meant a $C_1$ to $C_7$, preferably $C_1$ to $C_4$, alkanoic acid moiety, i.e., radicals of the formula

wherein R is $C_1$–$C_6$ or hydrogen e.g., acetyl, propionyl, butyryl and the like.

The expression "pharmaceutically acceptable salts" is used to include salts with both inorganic and organic pharmaceutically acceptable strong acids, such as, sulfonic acid, hydrochloric acid, nitric acid, methanesulfonic acid and p-toluene sulfonic acid. Such salts can be formed quite readily by those skilled in the art with the prior art and the nature of the compound to be placed in salt form in view.

Preferred compounds include those wherein A is the group (a) above and n is 0.

Within the above limitation particularly preferred compounds are those wherein

—$R_2$ and $R_3$ are hydrogen and $R_1$ is selected from the group consisting of hydrogen, lower alkyl, the group $NR_4R_5$ (wherein $R_4$ and $R_5$ are hydrogen or lower alkyl), hydroxy, chlorine, bromine, the group —$NH$—$(CH_2)_mNR_8R_9$ (wherein $R_8$ and $R_9$ are lower alkyl) and the group —$CH_2$—CO—$R_7$ (wherein $R_7$ is as above);

—$R_2$ is hydrogen, $R_3$ is hydroxy and $R_1$ is hydrogen, lower alkyl, or the group $NR_4R_5$ (wherein $R_4$ and $R_5$ are hydrogen or lower alkyl) or —$R_1$ and $R_3$ are hydrogen and $R_2$ is amino or di-lower alkylamino with dimethylamino as most preferred.

Among the preferred compounds the substituents X and Y may be X as halogen (chlorine most preferred) and Y as hydrogen, chlorine or fluorine.

A particularly preferred compound of the invention is 9-chloro-7-(2-chlorophenyl)-5H-pyrimido[5,4-d][2]benzazepine.

Further examples of preferred compounds of the invention are

-9-chloro-7-(12-fluorophenyl)-5H-pyrimido[5,4-d][2]benzazepine;
-9-chloro-7-(2-chlorophenyl)-2-methyl-5H-pyrimido[5,4-d][2]benzazepine;
-9-chloro-7-(2-fluorophenyl)-N,N-dimethyl-5H-pyrimido[5,4-d][2]benzazepine-4-amine;
-9chloro-7-(2-fluorophenyl)-5H-pyrimido[5,4-d][2]benzazepin-2-ol; and
-9-chloro-N,N-dimethyl-7-(2-fluorophenyl)-5H-pyrimido[5,4-d][2]benzazepin-2-amine.

The following reaction schemes show different preparative routes to produce the novel end products of the present invention:

In accordance with the present invention, compounds of formula I and pharmaceutically acceptable acid addition salts thereof can be prepared by (a) cyclizing a compound of the general formula

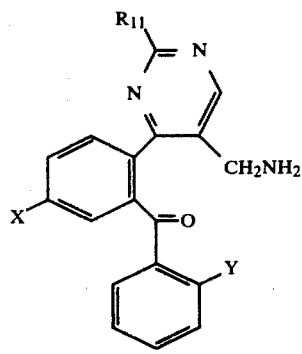

II wherein X and Y are as above and $R_{11}$ is hydrogen, lower alkyl or $NR_8R_9$ wherein $R_8$ and $R_9$ are as above, or (b) dehydrogenating a compound of the general formula

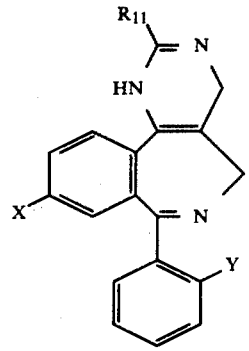

III

Wherein X, Y and $R_{11}$ are as above, or (c) reacting a compound of the general formula

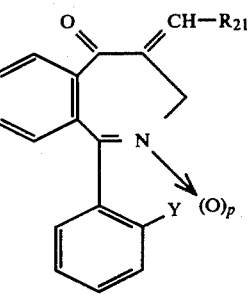

IV wherein X and Y are as above, p is 0 or 1 and $R_{21}$ represents di-lower alkyl amino, with cyanamide, or (d) reacting a compound of the general formula IV, above, with a compound of the general formula

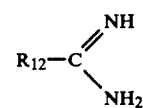

V wherein $R_{12}$ is hydrogen, mercapto, lower alkyl mercapto, lower alkyl or $NR_8R_9$ wherein $R_8$ and $R_9$ are as above, or (e) reducing a compound of the general formula

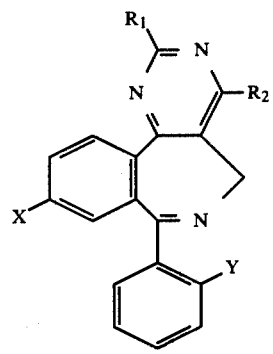

Ia wherein X, Y, $R_1$ and $R_2$ are as above, or (f) lower-alkylating a compound of the general formula

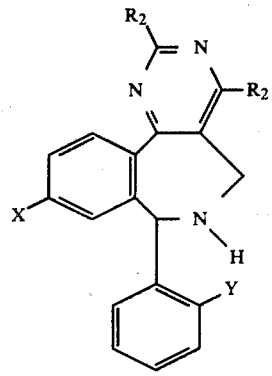

Ib wherein X, Y, $R_1$ and $R_2$ are as above, or (g) oxidizing a compound of the general formula

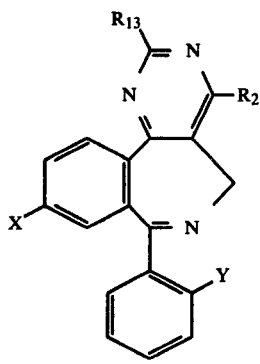

Ic wherein X, Y and $R_2$ are as above and $R_{13}$ represents hydrogen, lower alkyl, hydroxy, lower alkoxy, $NR_{41}R_{51}$ (wherein $R_{41}$ and $R_{51}$ each are hydrogen or lower alkyl or, together with the co-bonded nitrogen atom, represent a five to seven membered heterocycle which may contain an oxygen atom), chlorine, bromine or the group $-CH_2-CO-R_7$ (wherein $R_7$ is as above) with the proviso that at least one of $R_{13}$ and $R_2$ must be hydrogen, or (h) lower alkylating a compound of the general formula

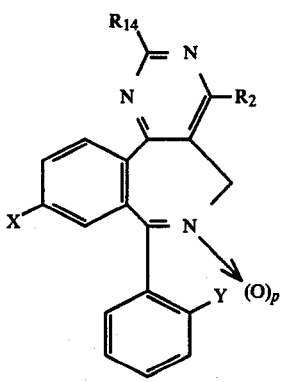

Id wherein X, Y and p are as above and $R_{14}$ represents mercapto or hydroxy, (i) converting a compound of the general formula

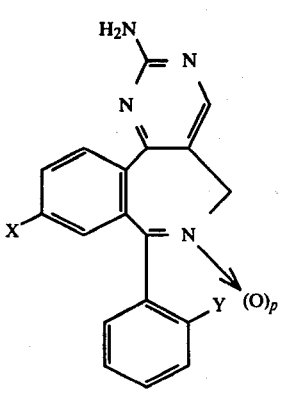

Ie wherein X, Y and p are as above, into the corresponding 2-hydroxy compound, or (k) converting a compound of the general formula

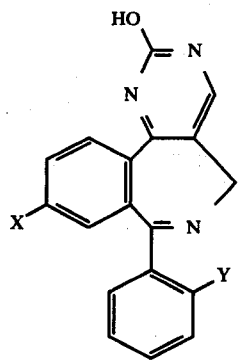

If wherein X and Y are as above, into a corresponding 2-chloro or bromo compound, or (l) treating a compound of the general formula

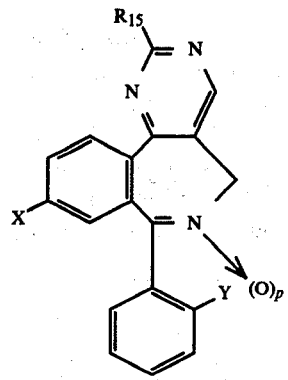

Ig wherein X, Y and p are as above and $R_{15}$ represents chlorine or bromine, with hydrogen sulfide, with a lower alkylmercaptan, with a lower alkanol, with a compound of formula $NR_4R_5$ wherein $R_4$ and $R_5$ are as above, with a compound of formula $H_2N-(CH_2)_mNR_8R_9$ wherein $R_8$, $R_9$ and m are as above or with the carbanion of a compound of the formula

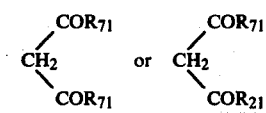

wherein $R_{71}$ is lower alkoxy and $R_{21}$ is as above, or (m) converting a compound of the general formula

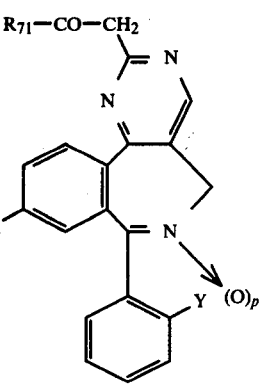

Ih wherein $R_{71}$, X, Y and p are as above, into the corresponding free acid or into a corresponding amide, lower alkyl amide or dilower alkyl amide, or (n) reacting a compound of the general formula

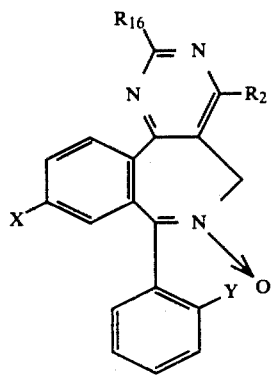

wherein Y and $R_2$ are as above, $R_{16}$ is hydrogen, chlorine, bromine, lower alkyl, the group $NR_4R_5$, the group —$CH_2$—CO—$R_7$, the group —$NH(CH_2)_mNR_{81}R_{91}$, hydroxy, lower alkoxy, mercapto or lower alkylmercapto, X' is hydrogen, halogen, trifluoromethyl, ethyl or acetyl, $R_{81}$ and $R_{91}$ each are lower alkyl and $R_4$, $R_5$ and $R_7$ are as above, with the proviso that at least one of $R_{16}$ and $R_2$ is hydrogen, with a lower alkylating agent or (o) hydrolyzing a compound of the general formula

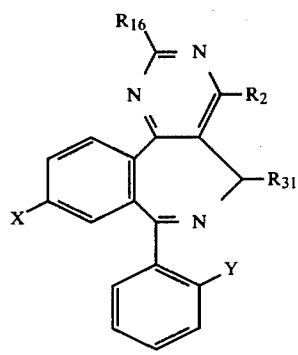

wherein X', Y, $R_{16}$ and $R_2$ are as above and $R_{31}$ is lower acyloxy, with the proviso that at least one of $R_{16}$ and $R_2$ is hydrogen, or (p) deoxygenating a compound of the general formula

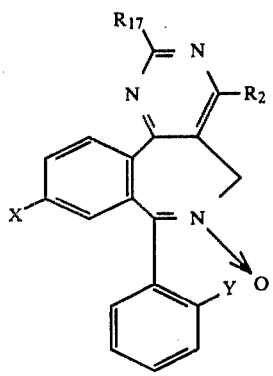

wherein X, Y, and $R_2$ are as above, $R_{17}$ is hydrogen, lower alkyl, the group $NR_4R_5$, the group —$CH_2$—CO—$R_7$, the group $NH$—$(CH_2)_m$—$NR_8R_9$, hydroxy, lower alkoxy, mercapto or lower alkylmercapto and $R_4$, $R_5$, $R_7$, $R_8$ and $R_9$ are as above, with the proviso that at least one of $R_{17}$ and $R_2$ is hydrogen, (q) removing the elements of H-Z from a compound of the general formula

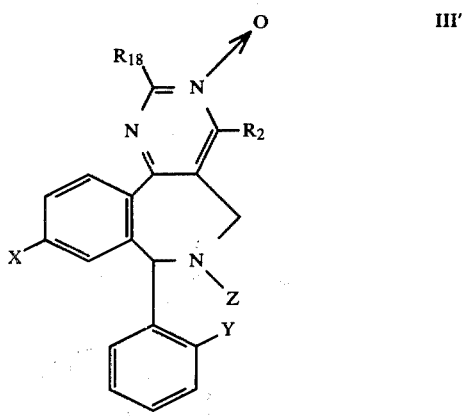

wherein X, Y and $R_2$ are as above, $R_{18}$ is hydrogen, lower alkyl, lower alkoxy, chlorine, bromine or the group —$CH_2$—CO—$R_7$ (wherein $R_7$ is as above) and Z represents hydrogen or an easily cleavable acyl group or sulfonamide with the proviso than at least one of $R_{18}$ and $R_2$ is hydrogen, or (r) converting a compound of formula I into a pharmaceutically acceptable acid addition salt.

It will be appreciated and readily apparent to those skilled in the art that when the compound to be subjected to any of the aforementioned reactions contains, in addition to group(s) involved in the reaction, groups which may be vulnerable under the conditions of such reaction, such vulnerable group has to be protected before carrying out the reaction and thereafter the protecting group has to be removed. This may be accomplished by utilizing well-known protecting groups and methods known in the art.

Process embodiments (a) and (b), above, and the preparation of the starting materials therefor are, by way of example, illustrated by the following Reaction Scheme I wherein X, Y and $R_{11}$ are as above:

Reaction Scheme I

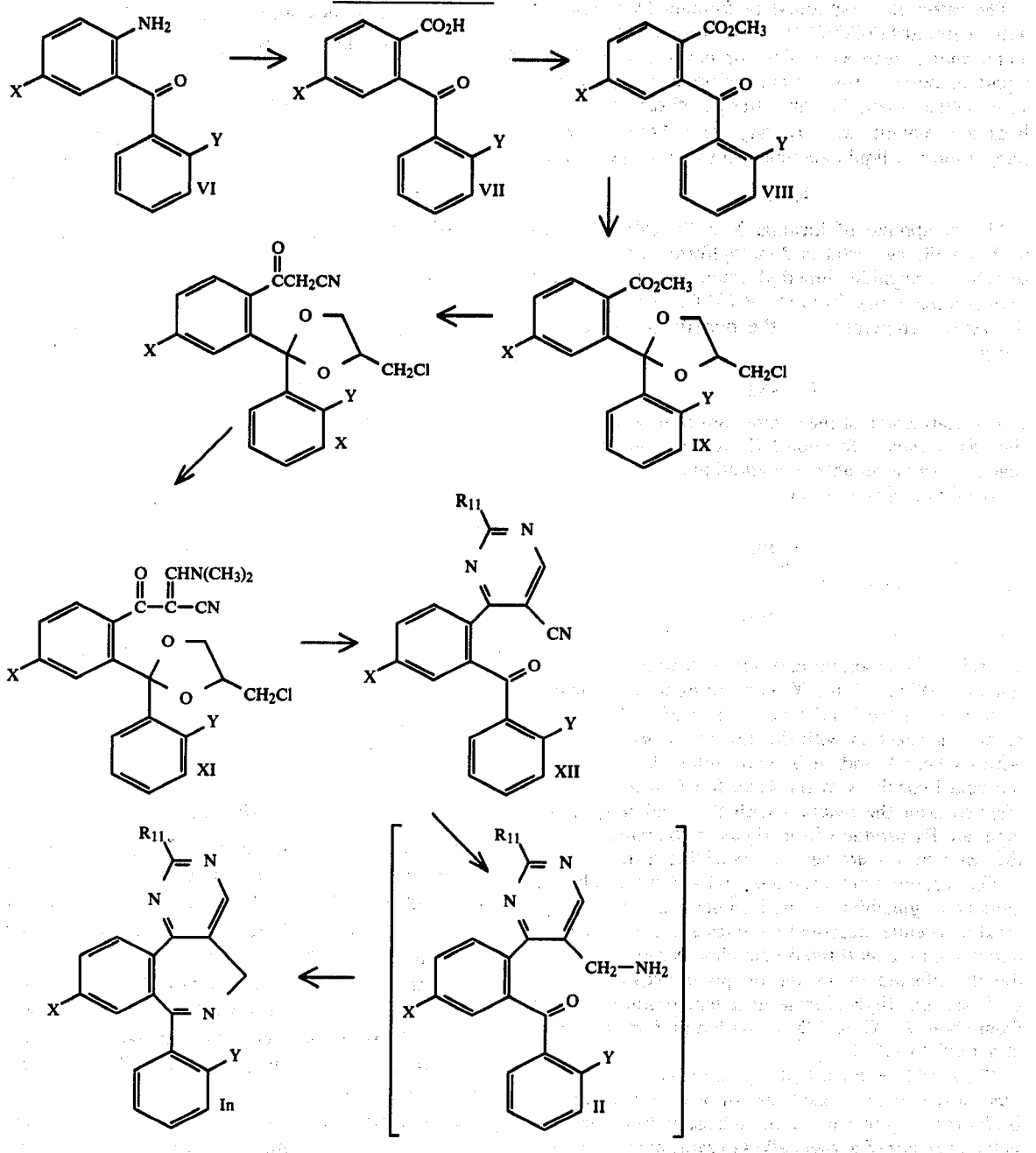

The compounds VI, VII and VIII are generically known in the art. A method to produce them is included for completeness of disclosure.

VI→VII

The compound of formula VI which is a well-known prior art compound is reacted with cuprous cyanide after being previously treated with sulfuric acid, sodiun nitrite and optionally sodium tetrafluorborate in seriatium. Thereafter the mixture is hydrolysed with an alkali metal hydroxide, e.g., sodium or potassium hydroxide at reflux temperatures.

VII→VIII

The compound of formula VIII is formed by the reaction of the carboxylic acid of formula VII which methanol in the presence of an acid catalyst, such as, sulfuric acid at about the reflux temperature of methanol for about 3 to 18 hours.

VIII→IX

The compound of formula VIII is thereafter reacted with 1-chloro-2,3-epoxy propane or other suitable epoxide ketalizing reagents such as ethylene oxide and 1,2-epoxypropane in the presence of a Lewis acid, such as, aluminum chloride or boron trifluoride or preferably stannic chloride in an inert organic solvent, such as, toluene, carbon tetrachloride, or benzene. Suitable reaction temperatures range from about 20° C. to 110° C. with about 25° C. being preferred.

IX→X

Thereafter the compound of formula IX is reacted with acetonitrile (CH3CN) in the presence of an alkali metal amide, such as, sodium or potassium amide, in liquid ammonia in the presence of an inert organic solvent, such as, diethyl ether, tetrahydrofuran or dioxane. Reaction temperature may vary from about the reflux temperature of liquid ammonia to room temperature.

X→XI

The compound of formula X is thereafter reacted with a dialkoxy acetal of dimethylformamide, such as, dimethylformamide dimethylacetal. Suitable reaction temperatures range from about 25° C. to 120° C. with the reflux temperature of the dimethylacetal as preferred.

XI→XII

The conversion of the compounds of formula XI into the compounds of formula XII involves two steps, viz. reaction with a suitable acid addition salt of an amidine or guanidine of the formula

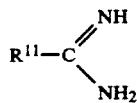

Va wherein $R^{11}$ is as above, and acid hydrolysis of the ketal function. Where X and Y both are hydrogen, the acid hydrolysis of the ketal function is preferably effected before the reaction with the amidine or guanidine salt whilst where X and/or Y is/are other than hydrogen, the acid hydrolysis of the ketal function is preferably effected after the reaction with the amidine or guanidine salt. By-products formed have to be removed from the reaction mixture before proceeding further.

The reaction with a suitable acid additional salt of an amidine or guanidine of the formula Va, such as, formamidine acetate, acetamidine hydrochloride, guanidine carbonate or a substituted guanidine carbonate is expediently effected in an aprotic polar organic solvent, such as, dimethylsulfoxide at a temperature range of from about 25° C. to 125° C. with a preferred range of about 90° to 95° C.

The ketal function is hydrolysed by means of an aqueous inorganic acid, such as, sulfuric, phosphoric or preferably a hydrohalic acid, such as, hydrochloric acid in the presence of a lower alkyl organic alcohol solvent, preferably, ethanol. The reaction is run at about room temperature.

XII→II

The compound of formula II is formed by the hydrogenation of the compound of formula XII in the presence of a metal catalyst such as platinum, palladium or Raney nickel and cyclizes spontaneously to give compound In. The hydrogenation may be carried out in a suitable organic solvent such as lower alkyl organic alcohols or lower alkyl carboxylic acids, i.e., acetic acid. Depending on the conditions used in the aforementioned hydrogenation, a dihydro pyrimido compound of formula III may be formed in addition to, or instead of, the compound of formula In. This dihydropyrimido compound may be converted into the compound of formula In by treatment with a mild oxidizing agent, such as, manganese dioxide, air and the like.

Process embodiment (c) is, by way of example, illustrated by the following Reaction Scheme II:

Reaction Scheme II

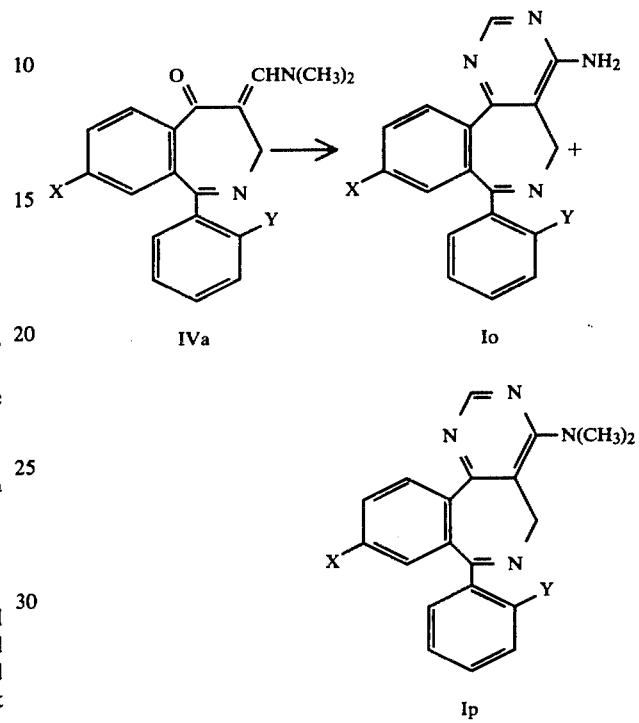

IVa→Io and Ip

The compound of the formula IVa is known in the prior art, see, for example, U.S. Pat. Nos. 3,947,585; 4,022,800 and 4,028,381. The compound is reacted with cyanamide in a $C_1$ to $C_4$ alcohol, e.g., ethanol, at a temperature range of about 25° C. to 80° C. with a preferred temperature at reflux of the particular alcohol chosen.

There is obtained a mixture of the amino compound and the N,N-disubstituted amino compound which can be separated by, e.g. fractional crystallization and/or chromatography.

Process embodiment (d), above, involves the reaction of a compound of formula IV with an amidine or guanidine or salt thereof or with thiourea or an S-lower alkyl isothiourea. For the reaction with the amidine or guanidine or salt thereof, any inert organic solvent such as dioxane, tetrahydrofuran or dimethylformamide may be utilized with a reaction temperature ranging from about room temperature to reflux temperature of the solvent with about room temperature as preferred. The reaction with thiourea or with an S-lower alkyl isothiourea can be effected in the presence of alcoholic e.g., methanolic, solution of an alkali metal alkoxide, e.g. sodium methoxide. The reaction may be carried out at from about 0° C. to 65° C. with about room temperature as preferred.

Process embodiments (e) and (f) are, by way of example, illustrated by the following Reaction Scheme III, wherein $R_{11}$ is as above:

Reaction Scheme III

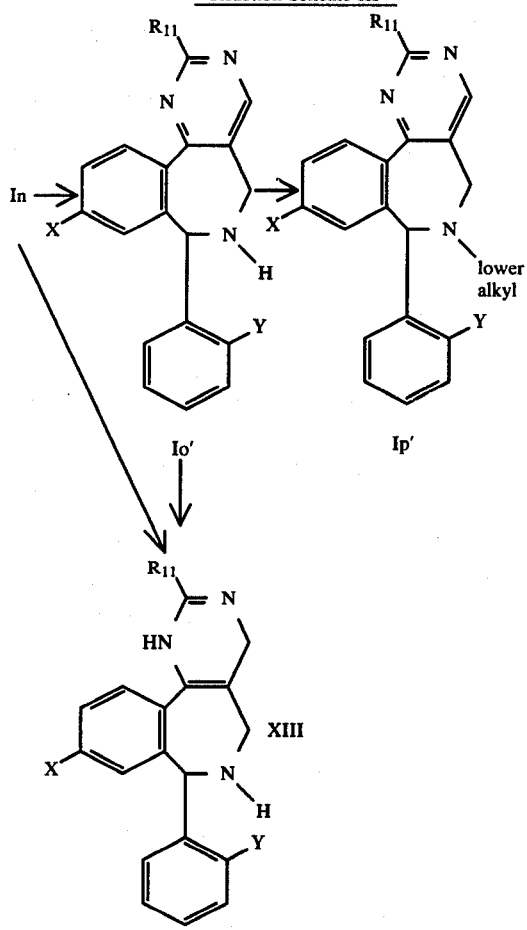

In→Io′ and In or Io′→XIII

The compound of formula In (see Reaction Scheme I) is treated with a reducing agent such as zinc in acetic acid at a reaction temperature of about −40° C. to 20° C. to give Io. The solvent utilized may be a halogenated hydrocarbon such as methylene chloride.

The compound of formula In or Io′ is reacted with hydrogen in the presence of platinum oxide or prehydrogenated platinum oxide and as a solvent acetic acid to give XIII. The reaction is normally run at about room temperature.

Other useful reducing agents for process embodiment (e) include sodium cyanoborohydride, sodium borohydride and the like.

In many instances, mixtures of the 6,7-dihydro and the 4,5,6,7-tetrahydro compounds are obtained. The said 4,5,6,7-tetrahydro compounds also exhibit useful CNS properties.

Io′→Ip′

The compound of formula Io′ is reacted with formaldehyde in formic acid with heating, e.g. about reflux temperature to methylate the dihydro compound. Methylation can also be accomplished with e.g. methyl iodide, dimethylsulfate or the like.

Lower alkyl substituents other then methyl may be produced by utilizing the appropriate alkyl halides, sulfates, alkylsulfonates, tosylates or the like in a solvent, such as, dimethylformamide, tetrahydrofuran, glyme and diglyme, or etherial solvents or by utilizing the appropriate aldehydes under reducing reaction conditions.

Process embodiments (g) is, by way of example, illustrated by the following Reaction Scheme IV wherein $R_{11}$ is as above:

Reaction Scheme IV

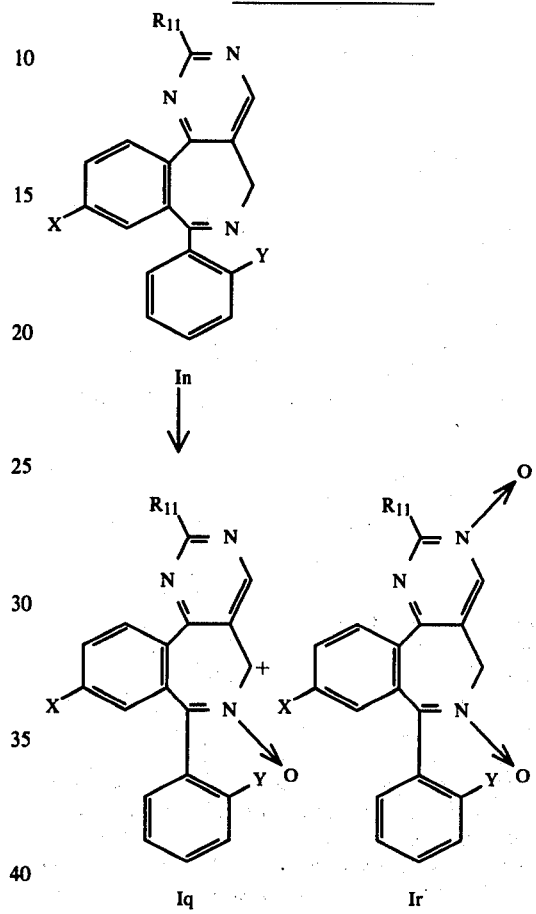

The compound of formula In is reacted with a suitable oxidizing agent such as metachloroperbenzoic acid in an inert organic solvent, such as, methylene chloride. The reaction may be run at between about 0° C. to room temperature with about room temperature as preferred. The reaction time may be varied depending an whether the N-oxide or di-N-oxide product is desired. The N-oxide Iq is produced predominantly where the reaction time is varied between about 2 and 25 hours whereas the di-N-oxide Ir is produced in predominance where the reaction time is between about 40 and 60 hours.

According to process embodiment (h), above, a mercapto or hydroxy group is lower alkylated according to methods known per se. The alkylation of the mercapto group is expediently effected by means of an appropriate alkyl halide in the presence of a mixture of an alkali metal hydroxide, such as, sodium hydroxide and a $C_1$ to $C_4$ alcohol, such as, ethanol. The reaction may be carried out preferably at about room temperature.

The alkylation of the hydroxy group is expediently effected with a dialkyl sulfate such as, dimethyl or diethyl sulfate in the presence of basic conditions, e.g., with sodium hydroxide present. The reaction may be run at from about 0° C. to 65° C. with about room temperature as preferred.

The conversion of a 2-amino compound into the corresponding 2-hydroxy compound according to process embodiment (j), above, can be effected by means of an acid, such as, sulphuric acid. The reaction temperature may be varied from about 25° C. to 125° C. with about 100° C. as the preferred temperature.

Other methods which may be used for this conversion include alkaline hydrolysis and displacement of diazonium salts.

The conversion of a 2-hydroxy compound into the corresponding 2-chloro or bromo compound according to process embodiment (k), above, can be effected, respectively, with a suitable chlorinating agent, such as, phosphorus trichloride at reflux temperature of the mixture, and with a suitable brominating agent, such as, phosphoryl bromide or phosphorus pentabromide at from about room temperature to reflux.

According to process embodiment (1), above, the chlorine or bromine atom in position 2 of the compound of formula Ig can be displaced by nucleophilic substitution with a number of heteroatom and carbon atom nucleophiles such as methanol, 3-dimethylaminopropylamine, methylamine, dimethylamine, N-methylpiperazine, the carbanion of diethylmalonate and the like, in an inert polar organic solvent, such as, dimethylformamide at from 0° C. to reflux temperature of the solvent, preferably at room temperature of the solvent.

The conversion of a compound of formula Ih into the corresponding free acid according to process embodiment (m), above, is expediently effected by hydrolysis under alkaline conditions, e.g. by means of an alkali or earth alkali metal hydroxyde, such as, sodium or potassium hydroxide or the like, in the presence of a suitable solvent such as a lower alkanol, e.g. ethanol.

The conversion of a compound of formula Ih into a corresponding amide according to process embodiment (m), above, can be effected either by treatment with ammonia or an appropriate mono- or di-lower alkylamine at room temperature or at an elevated temperature (suitably about 50°-130° C.), in the presence of an inert organic solvent such as a lower alkanol, e.g. ethanol, or by a hydrolysis to the corresponding free acid, conversion of the free acid into a reactive derivative, such as an acid chloride or a mixed anhydride, and subsequent treatment of this reactive derivative with ammonia or an appropriate mono- or di-lower alkylamine.

Process embodiment (n) and (o) are by way of example illustrated by the following Reaction Scheme V wherein X', Y, $R_{11}$ and $R_{11}$ are as above:

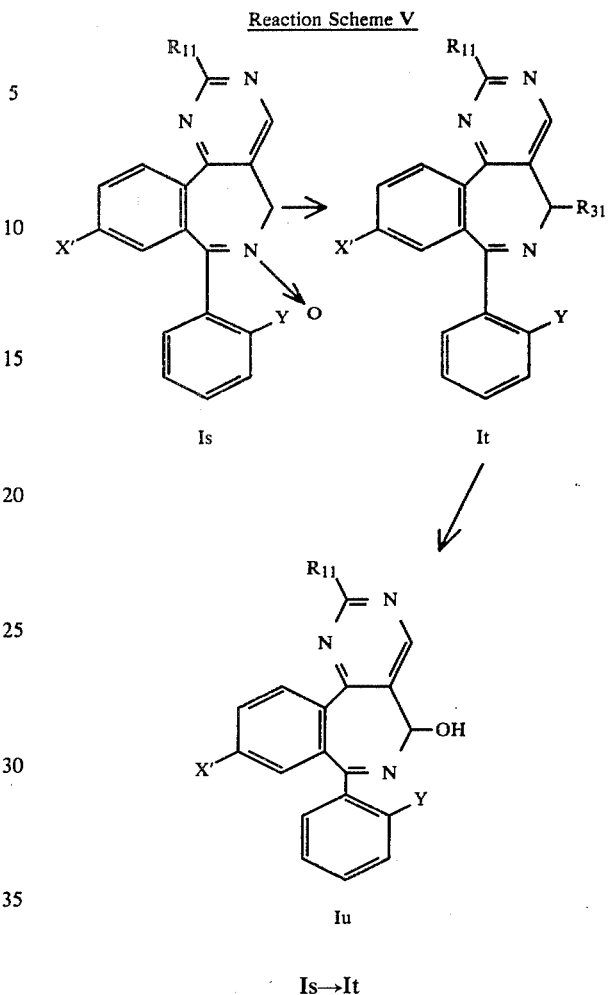

Reaction Scheme V

Is→It

The compound of formula Is can be reacted with an acid anhydride of a suitable carboxylic acid such as acetic- or trifluoroacetic-anhydride. The reaction is preferably done at about the reflux temperature of the anhydride chosen. Instead of an acid anhydride, also an acid chloride can be utilized.

It→Iu

The compound of formula It can be reacted with an alkali metal carbonate, such as, sodium or potassium carbonate, in a $C_1$ to $C_4$ alcohol, such as, methanol at a temperature range of about 0° C. to 65° C. with about room temperature as preferred. Other reaction conditions suitable for this step include the use of alkali metal hydroxides, e.g., sodium or potassium hydroxide, and a $C_1$ to $C_5$ alcohol in the presence of water or, in the alternative, an acid hydrolysis utilizing an aqueous mineral acid such as hydrochloric or sulfuric acid with a solvent such as THF or dioxane with a reaction temperature from about 0° C. to room temperature with 0° C. as preferred.

The deoxygenation according to process embodiment (p), above, can be effected by methods known per se, e.g. by means of reagents such as phosphorus trichloride, tri-lower alkyl phosphites (e.g. triethyl phosphite), hexachlorodisilane, Raney-nickel and the like.

Process embodiment (q), above, and the preparation of the starting materials therefor are, by way of example, illustrated by the following Reaction Scheme VI, wherein X, Y and $R_{18}$ are as above and Z' represents an easily cleavable acyl or sulfonamide group:

rying out an acylation or sulfonation of this kind will be readily apparent to those skilled in the art.

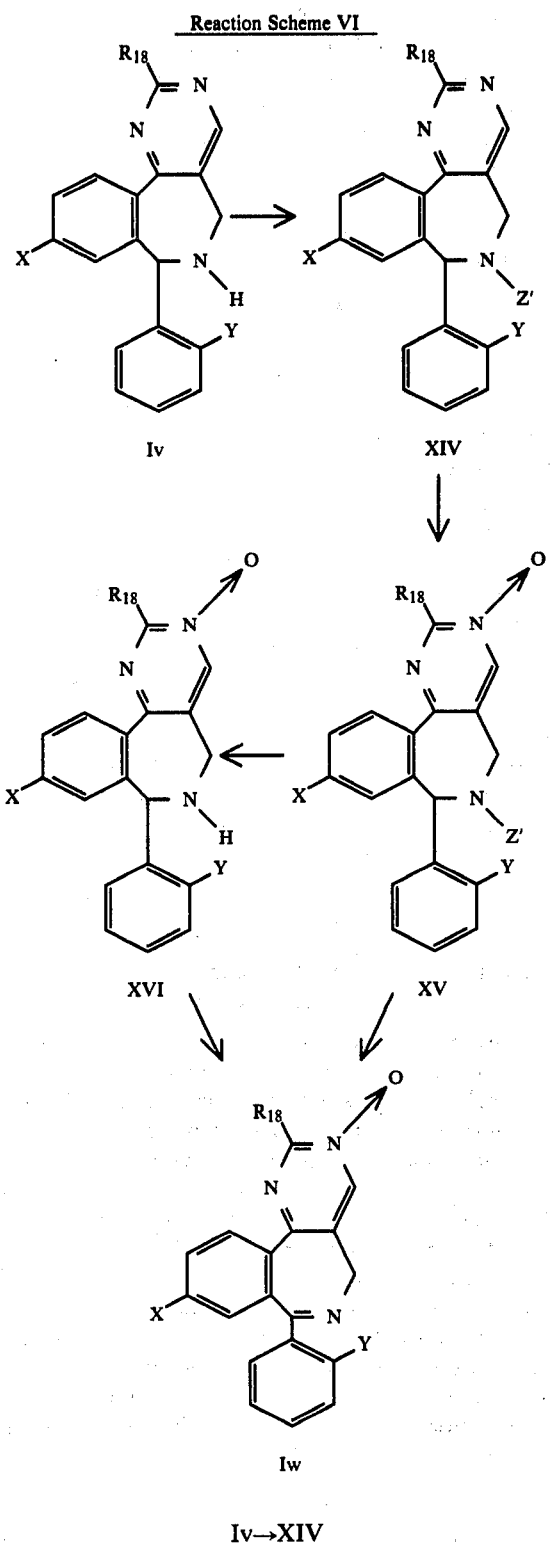

XIV→XV

The compound of formula XIV is reacted with a suitable oxidizing agent such as metachloroperbenzoic acid in an inert organic solvent, such as, methylene chloride. The reaction may be run at between about 0° C. to about room temperature with about room temperature as preferred. The reaction time is between about 40 to 60 hours.

XV→XVI

The acyl group Z' is split off by methods known per se which are readily apparent to those skilled in the art. The choice of the method to be utilized depends of course, from the nature of the acyl group Z'. Thus, for example, the trifluoroacetyl or ethoxycarbonyl groups can be removed by alkaline hydrolysis, the formyl group by acid hydrolysis and the benzyloxycarbonyl group by means of hydrogen bromide etc.

XVI or XV→Iw

The conversion of XVI into Iw involves a dehydrogenation which can be effected by methods known per se, e.g. by means of diethylazodicarboxylate or by N-halogenation (preferably N-bromination) followed by a dehydrohalogenation under alkaline conditions, e.g. by means of a tertiary amine such as triethylamine.

When Z' in formula XV is a group such as tosyl or mesyl, there can be carried out an elimination of H—Z' under alkaline conditions, e.g. by means of an alkali metal alkoxide in the corresponding alkanol, such as, methanolic sodium methoxide.

Any 7H-isomer of the compound of formula Iw formed can be isomerised to the compound of formula Iw by treatment with a suitable base, e.g. methanolic sodium methoxide.

For the sake of completeness, the preparation of those among the intermediates of formula IV wherein p is 1 is, by way of example, illustrated by the following Reaction Scheme VII wherein X and Y are as above:

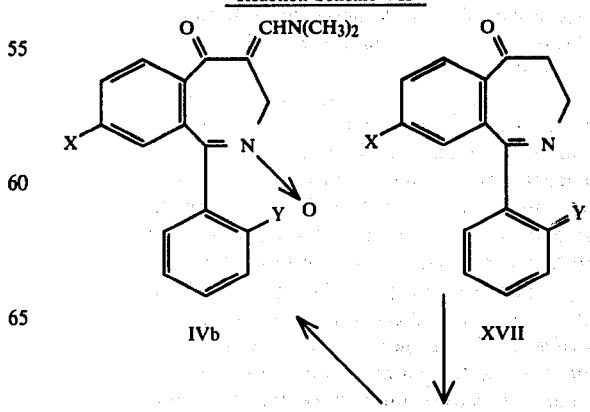

Iv→XIV

This conversion involves protection of the amino group with a suitable acylating or sulfonating agent to yield the easily cleavable protecting group Z', such as trifluoroacetylchloride, p-toluenesulfonylchloride, methanesulfonylchloride, the mixed anhydride of formic acid and acetic acid, ethyl chloroformate, benzyloxycarbonylchloride and the like. The conditions for car- -continued
Reaction Scheme VII

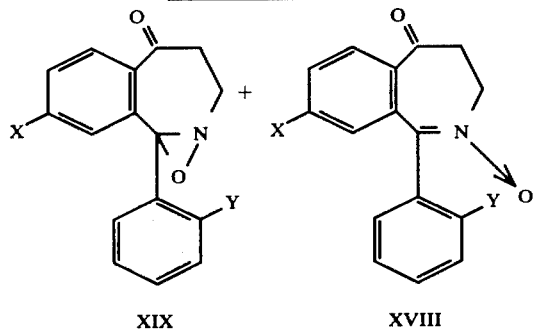

XIX            XVIII

The compound of formula XVII can be reacted with a peracid such as, metachloroperbenzoic acid in an inert organic solvent such as a halogenated hydrocarbon, e.g. methylene chloride, or an ether. The reaction may be carried out from about 0° C. to 40° C. with room temperature as preferred. The mixture of products may thereafter be separated from one another by fractional crystallization. Analysis by thin-layer chromatography indicates the presence of both products.

The compounds of formula XVIII can be reacted with dimethylformamide dimethylacetal in an inert solvent, such as, a halogenated hydrocarbon, e.g. methylene chloride, or dimethylformamide or high boiling ethers. The reaction temperature may range from about 0° C. to 100° C. with room temperature as preferred.

The pyrimido-2-benzazepines of formula I, above, and their pharmaceutically acceptable acid addition salts, are useful as pharmaceuticals and are characterized by activity as sedative and anxiolytic agents. These compounds can be used in the form of conventional pharmaceutical preparations; for example, the aforesaid compounds can be mixed with conventional organic or inorganic, inert pharmaceutical carriers suitable for parenteral or enteral administration such as for example, water gelatin, lactose, starch, magnesium stearate, talc, vegetable oil, gums, polyalkylene glycols, Vaseline or the like. They can be administered in conventional pharmaceutical forms, e.g., solid forms, for example, tablets, dragees, capsules, suppositories or the like, or in liquid forms, for example, solutions, suspensions or emulsions. Moreover, the pharmaceutical compositions containing compounds of this invention can be subjected to conventional pharmaceutical expedients such as sterilization, and can contain conventional pharmaceutical excipients such as preservations, stabilizing agents, wetting agents, emulsifying agents, salts for the adjustment of osmotic pressure, or buffers. The compositions can also contain other therapeutically active materials.

A suitable pharmaceutical dosage unit can contain from about 1 to about 500 mg of a compound of formula I or a pharmaceutically acceptable acid addition salt thereof with a dosage range of from about 1 mg to about 100 mg being the preferred oral administration and a dosage range of from about 1 mg to about 50 mg being preferred for parenteral administration. However, for any particular subject, the specific dosage regimen should be adjusted according to individual need and the professional judgment of the person administering or supervising the administration of the aforesaid compounds. It is to be understood that the dosages set forth herein are exemplary only and that they do not, to any extent, limit the scope or practice of this invention.

The term "dosage unit" as employed throughout this specification refers to pharmaceutically discrete units suitable as unitary dosages for mammalian subjects each containing a predetermined quantity of active material calculated to produce the desired therapeutic effect in association with the required pharmaceutical diluent, carrier or vehicle.

The following examples are illustrative, but not limitative of this invention. All temperatures given are in degrees centigrade, unless indicated otherwise.

EXAMPLE 1

2-Amino-9-chloro-7-phenyl-5H-pyrimido[5,4-d][2]benzazepine

A stirred suspension of 10 g (0.032 mol) of 8-chloro-3,4-dihydro-4-(dimethylaminomethylene)-1-phenyl-5H-2-benzazepin-5-one and 8.5 g (0.047 mol) of guanidine carbonate in 250 ml of methanol was treated at room temperature, under argon, with 5.1 g (0.094 mol) of sodium methylate in one portion. Methylene chloride (150 ml) was added after 10 min and stirring was continued. The same quantities of sodium methylate and guanidine carbonate were added two more times at 2 hr intervals and stirring was continued overnight. After diluting with 250 ml of methylene chloride, the mixture was washed with water, dried over sodium sulfate and evaporated at reduced pressure. Crystallization of the residue from ethanol gave light tan crystals: mp 209°–210° C. Recrystallization of a sample from methylene chloride/ethyl acetate gave off-white prisms: mp 210°–211° C.

EXAMPLE 2

2-Amino-9-chloro-7-(2-fluorophenyl)-5H-pyrimido[5,4-d][2]benzazepine

A stirred suspension of 16 g (0.047 mol) of 8-chloro-1-(2-fluorophenyl)-3,4-dihydro-4-[(dimethylamino)methylene]-5H-2-benzazepin-5-one and 12.5 g (0.07 mol) of guanidine carbonate in 460 ml of methanol was treated at room temperature, under argon, with 7.5 g (0.14 mol) of sodium methylate in one portion. Methylene chloride (290 ml) was added after 10 min. and stirring was continued. The same quantities of sodium methylate and guanidine carbonate were added two more times at 2 hr intervals and stirring was continued overnight. After diluting with 460 ml of methylene chloride, the mixture was washed with water, dried over sodium sulfate and evaporated at reduced pressure. Recrystallization of the residue from ethanol/methylene chloride solution gave off-white crystals: mp 245°–248° C.

Dihydrochloride salt

A warm solution of the above end product in 100 ml of 1:1 methanol/methylene chloride was filtered and concentrated on a steam bath to ½ volume. The filtrate was treated with 5 ml of 5.7 N ethanolic hydrogen chloride solution and kept at room temperature for 2 hr. The pale yellow crystals were filtered, washed with ethanol and air dried to yield the dihydrochloride salt: mp 232°–237° C.

EXAMPLE 3

9-Chloro-2-methyl-7-phenyl-5H-pyrimido[5,4-d][2]benzazepine

A suspension of 1.6 g (0.005 mol) of 8-chloro-3,4-dihydro-4-(dimethylaminomethylene)-1-phenyl-5H-2-benzazepin-5-one and 0.7 g (0.0075 mol) of acetamidine hydrochloride in 50 ml of methanol was stirred at room temperature, under argon, and treated with 0.8 g (0.015 mol) of sodium methylate in one portion. After stirring for 10 min, 30 ml of methylene chloride was added and stirring was continued. Another 0.8 g (0.015 mol) of sodium methylate and 0.7 g (0.0075 mol) of acetamidine hydrochloride were added after 2 hrs. The addition of 0.015 mol of sodium methylate and 0.0075 mol of acetamidine hydrochloride was repeated after another 2 hr and stirring at room temperature was continued overnight. After diluting with 50 ml of methylene chloride, the mixture was washed with water, dried over sodium sulfate and evaporated at reduced pressure. Crystallization occurred when the residue was dissolved in 20 ml of warm hexane and cooled. Evaporation of the solvent gave a second crop of product. Recrystallization from hexane (charcoal) gave off-white crystals: mp 120°–122° C.

EXAMPLE 4

9-Chloro-7-(2-fluorophenyl)-2-methyl-5H-pyrimido[5,4-d][2]benzazepine

A suspension of 5.1 g (0.015 mol) of 8-chloro-1-(2-fluorophenyl)-3,4-dihydro-4-[(dimethylamino)methylene]-5H-2-benzazepin-5-one and 2.1 g (0.0225 mol) of acetamidine hydrochloride in 150 ml of methanol was stirred at room temperature under argon, and treated with 2.4 g (0.045 mol) of sodium methylate in one portion. After stirring for 10 min, 90 ml of methylene chloride was added and stirring was continued. Another 2.4 g (0.045 mol) of sodium methylate and 2.1 g (0.0225 mol) of acetamidine hydrochloride were added after 2 hrs. The addition of 0.045 mol of sodium methylate and 0.0225 mol of acetamidine hydrochloride was repeated after another 2 hr interval and stirring at room temperature was continued overnight. After diluting with 150 ml of methylene chloride, the mixture was washed with water, dried over sodium sulfate and evaporated at reduced pressure. Recrystallization of the residue from hexane (charcoal) gave white crystals: mp 104°–107° C.

Example 5

9-Chloro-7-(2-fluorophenyl)-5H-pyrimido[5,4-d][2]benzazepin-2-amine and 9-chloro-7-(2-fluorophenyl)-N,N-dimethyl-5H-pyrimido[5,4-d][2]benzazepin-2amine A solution of 7.0 g (0.0204 mol) of 8-chloro-1-(2-fluorophenyl)-3,4-dihydro-4-[(dimethylamino)methylene]-5H-2-benzazepin-5-one and 3.5 g (0.0833 mol) of cyanamide in 300 ml of absolute ethanol was refluxed for 18 hours, and evaporated to dryness. The residue was washed with water, filtered and recrystallized twice from methanol to give the N,N-dimethyl amino compound. The filtrates were concentrated, filtered and recrystallized from methanol to give the amino compound. The filtrates were evaporated, dissolved in dichloromethane and chromatographed over Florisil. The column was eluted with dichloromethane which was evaporated and crystallized from methanol to give further N,N-dimethyl amino compound. A sample was crystallized from dichloromethane/ether to give white needles: mp 175°–180° C.

The column was next eluted with a 5% solution of ether in dichloromethane, and then with ether. The ether fraction was evaporated and crystallized from methanol to give further amino compound. A sample wasrecrystallized from methanol to give white prisms: mp 242°–247° C.

To a solution of 0.2 g (0.5 mmol) of the N,N-dimethyl amino compound in 5 ml of methanol was added 0.05 g (0.5 mmol) of methane sulfonic acid. The methanol was evaporated and the oil was crystallized from isopropanol and recrystallized from methanol/ether to give yellow prisms: mp 190°–195° C.

EXAMPLE 6

2-(2-Fluorobenzoyl)-4-chlorobenzoic acid, methyl ester

A solution of 2.0 g (7.19 mmoles) of [2-(2-fluorobenzoyl)-4-chlorobenzoic acid], in 40 ml of methanol and 0.3 ml of sulfuric acid was refluxed for 10 hrs and then evaporated. The residue was partitioned between 50 ml of dichloromethane and 30 ml of dilute ammonium hydroxide, and the organic layer was dried and evaporated. The resulting oil was dissolved in 20 ml of dichloromethane, filtered through 25 g of Florisil and eluted with dichloromethane. The solvent was evaporated and the oil was crystallized from ether and recrystallized from dichloromethane/ether/petrol to give white rods: mp 115°–116° C.

EXAMPLE 7

4-Chloro-2-[4-(chloromethyl)-2-(2-fluorophenyl)-1,3-dioxolan-2-yl]benzoic acid methyl ester To a solution of 47 g (0.16 mol) of the end product of Example 6 in 350 ml of dry toluene was added 21.4 ml (0.18 mol) of stannic chloride, and after 5 hrs a solution of 24 ml (0.308 mol) of 1-chloro-2,3-epoxypropane in 25 ml of toluene was added with stirring over a 30 min period. After 18 hrs an additional 12 ml (0.154 mol) of 1-chloro-2,3-epoxypropane was added over a 15 min period. After 4 hrs the reaction was cooled in an ice bath and made basic with concentrated ammonium hydroxide. The reaction was filtered through celite, and the celite was washed with toluene. The combined filtrates were washed with 200 ml of water, dried over sodium sulfate, and evaporated. The resulting oil was dissolved in 100 ml of dichloromethane and chromatographed through 500 g of alumina. The column was eluted with 4 l of dichloromethane/petrol (2/1) to give an oil, which was about 90–95% pure by TLC. A sample was crystallized and recrystallized from ether/petrol to give white prisms: mp 117°–122° C.

EXAMPLE 8

2-[4-Chloromethyl-2-(2-fluorophenyl)-1,3-dioxolan-2-yl]-α[(di-methylamino)-methylene]-β-oxo-(4-chlorophenyl)propanenitrile To 800 ml of liquid ammonia was added a small piece of sodium and a few crystals of ferric nitrate. A total of 8.7 g (0.378 mol) of sodium was added with stirring over a 30 min period, and after 15 mins a solution of 20.1 ml (0.378 mol) of acetonitrile in 70 ml of ether was added over a 15 min period. After 10 mins a solution of 56 g (0.145 mol) of the end product of Example 7 in 250 ml of ether was added over a 10 min period. The reaction was stirred for 2 hrs, and then 700 ml of ether was added. After allowing the ammonia to evaporate overnight, ice was added and the reaction was acidified with acetic acid. It was neutralized with a saturated sodium bicarbonate solution, and the water was separated and extracted again with 500 ml of ether. The combined ether layers were washed with brine (200 ml), dried over sodium sulfate and evaporated to dryness. The crude oil was dissolved in 150 ml of dichloromethane and filtered through 400 g of Florisil. The column was eluted with 1.5 l of dichloromethane to give an oil, which was about 90–95% pure by TLC.

The 48 g of the oil was refluxed and stirred for 90 mins with N,N-dimethylformamide dimethylacetal and the mixture was then evaporated to dryness. The residue was triturated with 300 ml of ice water, which was then decanted. The remaining oil was dissolved in 300 ml of dichloromethane, washed with 200 ml of water, and then dried over sodium sulfate. The solution was evaporated and the residue was crystallized from dichloromethane/ether to give end product. The filtrates were evaporated, dissolved in 100 ml of dichloromethane and filtered through 300 g of Florisil. Elution with dichloromethane (400 ml) and ether (1.5 l) gave upon evaporation and then crystallization from dichloromethane/ether end product. The filtrates contained end product as an oil which was about 85% pure by TLC. An analytical sample was recrystallized from the same solvents to give off-white prisms, mp 143°–147° C.

EXAMPLE 9

2-Amino-4-[2-[4-(chloromethyl)-2-(2-fluorophenyl)-1,3-dioxolan-2-yl]-4-chlorophenyl]pyrimidine-5-carbonitrile To a solution of 1.0 g (0.00223 mol) of the end product of Example 8 in 8 ml of dry dimethylsulfoxide was added 4 g of molecular sieves (type 5A) and 0.7 g (0.00389 mol) of guanidine carbonate. The reaction was stirred at 90°–95° C. for 5 hrs, cooled and 50 ml of dichloromethane was added. The solution was decanted and the solids were washed with dichloromethane and water several times. The combined solutions were separated, and the organic layer was washed with dilute brine (2x), and then dried over sodium sulfate and concentrated to a small volume. This solution was developed on 4 silica gel thick layer plates in dichloromethane/ethyl acetate (3/1). The band at Rf 0.4 was removed, crystallized and recrystallized from methanol to give off-white prisms, mp 184°–191° C.

EXAMPLE 10

2-Amino-4-[2-(2-fluorobenzoyl-4-chlorophenyl]-pyrimidine-5-carbonitrile

A solution of 0.2 g (0.448 mmole) of the end product of Example 9 in 20 ml of methanol and 10 ml of 3N hydrochloric acid was refluxed for 20 mins and the solvent was evaporated. The residue was partitioned between 50 ml of dichloromethane and 30 ml of dilute ammonium hydroxide, and the organic layer was dried, concentrated and filtered through 15 g of Florisil. The column was eluted with 200 ml of ether which was concentrated, filtered and recrystallized from dichloromethane/ether/petrol to give white prisms, mp 153°–157° C.

EXAMPLE 11

2-Amino-9-chloro-7-(2-fluorophenyl)-5-pyrimido[5,4-d][2]benzazepine

A solution of 50 mg (0.142 mmole) of the end product of Example 10 in 10 ml of acetic acid was treated with ¼ spatula of Raney nickel, and hydrogenated for 2.5 hrs. The reaction was filtered through celite, evaporated, and partitioned between 30 ml of dichloromethane and 15 ml of dilute ammonium hydroxide. The organic layer was dried with sodium sulfate, evaporated and the residue was refluxed in ethanol for 1 hr, and then evaporated to dryness. The solid was dissolved in dichloromethane and developed on a thick layer silica gel plate in ethyl acetate/ethanol (20/1). The band of Rf 0.3 was removed and crystallized from ether to give white prisms, mp 243°–248° C., and a mixed mp of 244°–248° C. with authentic material obtained as in Example 2.

EXAMPLE 12

2-[4-(Chloromethyl)-2-phenyl-1,3-dioxolan-2-yl]benzoic acid, methyl ester

To a solution of 33 g (0.138 mol) of 2-benzoyl benzoic acid methyl ester in 200 ml of dry carbon tetrachloride was added 10.1 ml (0.13 mol) of 1-chloro-3,4-epoxypropane. The reaction was cooled in an ice bath and a solution of 1.5 ml (0.013 mol) of stannic chloride in 10 ml of carbon tetrachloride was added with stirring over a 20 min period. The reaction was allowed to stand over the weekend, and then the same quantities of 1-chloro-2,3-epoxy-propane and stannic chloride were added. After 18 hours the reaction was cooled in an ice bath, and neutralized with concentrated ammonium hydroxide. The precipitate was filtered off and washed with dichloromethane and the combined filtrates were washed with 150 ml of water, dried with sodium sulfate and evaporated. The resulting oil was dissolved in 100 ml of dichloromethane and chromatographed through 500 g of neutral alumina. Elution with 3 l of dichloromethane gave the end product as an oil which was about 95% pure by TLC. Crystallization and recrystallization of a small sample from ether/petrol gave white rods, mp 90°–91° C.

EXAMPLE 13

2-[4-(Chloromethyl)-2-phenyl-1,3-dioxolan-2-yl]-α-[(dimethylamino)methylene]-β-oxo-benzenepropanenitrile To a stirring solution of 75 ml of liquid ammonia was added a small piece of sodium and a few crystals of ferric nitrate. A total of 1.15 g (0.0502 mol) of sodium was added over a 20 min period, and after 5 mins a solution of 2.9 ml (0.050 mol) of acetonitrile in 10 ml of ether was added dropwise. A solution of 6.6 g (0.0198 mol) of the end product of Example 12 in 40 ml of ether was added dropwise, and after 2 hrs 100 ml of ether was added and the ammonia was allowed to evaporate. About 100 g of ice was added to the reaction, which was then acidified with acetic acid, followed by neutralization with a saturated solution of sodium bicarbonate. The water layer was separated and extracted once more with ether. The combined ether layers were washed with 100 ml of water, dried over sodium sulfate and evaporated. The oil was dissolved in 15 ml of dichloromethane and filtered through 100 g of Florisil. Elution with dichloromethane, and evaporation gave 2-[4-

(chloromethyl)-2-phenyl-1,3-dioxolan-2-yl]-β-oxo-benzenepropanenitrile which was used without further purification.

A solution of 20 g (0.0585 mol) of the above propanenitrile in 75 ml of N,N-dimethylformamide dimethylacetal was refluxed and stirred for 90 mins, and evaporated to dryness. The oil was triturated with ice water which was decanted, and the residue was partitioned between 150 ml of dichloromethane and 150 ml of water. The organic layer was dried with sodium sulfate, concentrated, and filtered through 150 g of Florisil. The column was eluted with ether which was evaporated, and the resulting oil was crystallized from ethanol to give end product. A sample was recrystallized from dichloromethane/ether to give white prisms, mp 107°-110° C.

EXAMPLE 14

2-amino-4-(2-benzoylphenyl)pyrimidine-5-carbonitrile and 1-oxo-3-phenyl-1H-indene-2-carbonitrile To a solution of 2.0 g (0.00504 mol) of the end product of Example 13 in 10 ml of dichloromethane was added 10 ml of methanol and 2 ml (0.0192 mol) of 9.6 N ethanolic hydrogen chloride. After 90 mins the solvent was evaporated and the oil was partitioned between 50 ml of dichloromethane and 30 ml of a saturated sodium bicarbonate solution. The organic layer was dried with sodium sulfate and evaporated. The 1.5 g of oil obtained was dissolved in 30 ml of methanol, and 1.5 g (0.00833 mol) of guanidine carbonate was added. The solution was stirred for 90 minutes and then refluxed for 2 hours. The reaction was evaporated and then partitioned between 50 ml of dichloromethane and 30 ml of dilute ammonium hydroxide. The organic layer was dried with sodium sulfate and filtered through 50 g of Florisil. The column was eluted with dichloromethane (200 ml) and then ether (300 ml). The dichloromethane fraction was evaporated, crystallized and then recrystallized from dichloromethane/petrol to give the indene as yellow rods, mp 173°-175° C.

The ether fraction was evaporated and crystallized from dichloromethane/petrol to give the pyrimidine mp 195°-199° C. An analytical sample was recrystallized from methanol to give off-white prisms, mp 197°-200° C.

EXAMPLE 15

7-phenyl-5H-pyrimido[5,4-d][2]benzazepin-2-amine

A solution of 3.1 g (0.0103 mol) of the pyrimidine compound of Example 14 in 60 ml of glacial acetic acid was treated with 1 teaspoon of Raney nickel and then hydrogenated for 8.5 hours. The reaction was filtered through celite, and evaporated. The filtrate was partitioned between 50 ml of dichloromethane and 30 ml of dilute ammonium hydroxide, and the organic layer was dried with sodium sulfate and evaporated. The resulting oil was refluxed in 75 ml of methanol for 15 minutes, evaporated and dissolved in 100 ml of dichloromethane. This was treated with 3 g of activated manganese dioxide, and then refluxed and stirred for 30 mins. The reaction was filtered, concentrated and chromatographed over 100 g of Florisil. The column was eluted with 300 ml of dichloromethane, 500 ml of ether and 1.5 l of ethyl acetate. The ethyl acetate fraction was evaporated, and the oil was crystallized from ether and recrystallized from dichloromethane/ether to give white rods, mp 239°-242° C. The filtrates and the ether fraction from the column were evaporated and developed on silica gel thick layer plates in ethyl acetate/methanol (20/1) to give additional product. An analytical sample was recrystallized from ether to give white prisms, mp 201°-205° C. which reset to form rods, mp 240°-243° C.

EXAMPLE 16

9-chloro-7-(2-chlorophenyl)-2-methyl-5H-pyrimido[5,4-d][2]benzazepine

In five equal portions 5.5 g (58 mmole) of acetamidine hydrochloride and 15 ml (62 mmole) of a 4.12 M methanol solution of sodium methoxide was added over 3 hr. to a solution of 3.5 g (10 mmole) of 8-chloro-1-(2-chlorophenyl)-3,4-dihydro-4-[(dimethylamino)methylene]-5H-2-benzazepin-5-one in 140 ml of methanol and 140 ml of methylene chloride. The mixture was diluted with water and extracted with methylene chloride. The methylene chloride solution was washed with water dried with anhydrous sodium sulfate, and concentrated at reduced pressure to give an amber oil. The amber oil was dissolved in 10 ml (10 mmole) of a 1 M methanol solution of methanesulfonic acid and the resulting salt was precipitated by the addition of ether to give yellow prisms, mp 193°-197° C. Recrystallization from a mixture of methanol and ether gave yellow prisms, mp 197°-198° C.

EXAMPLE 17

9-chloro-7-(2-chlorophenyl)-5H-pyrimido[5,4-d][2]benzazepine

In five equal portions 21 g (200 mmole) of formamidine acetate and 32.5 ml (135 mmole) of a 4.12 M methanol solution of sodium methoxide was added over 3 hr to a solution of 7.2 g (20 mmole) of 8-chloro-1-(2-chlorophenyl)-3,4-dihydro-[(dimethylamino)methylene]-5H-2-benzazepin-5-one in 270 ml of methanol and 270 ml of methylene chloride. The solution was diluted with water and extracted with methylene chloride. The methylene chloride solution was washed with water, dried over anhydrous sodium sulfate, and concentrated at reduced pressure to give an amber oil. Purification by column chromatography (100 g silica gel; eluent 1:1 methylene chloride and ethyl acetate) gave end poduct mp 122°-124° C. Recrystallization from ether gave pale yellow prisms, mp 122°-125° C.

EXAMPLE 18

9-chloro-7-(2-chlorophenyl)-2-isopropyl-5H-pyrimido[5,4-d][2]benzazepine

A mixture of 3.5 g (10 mmole) of 1-(2-chlorophenyl)-3,4-dihydro-4-[(dimethylamino)methylene]-5H-2-benzazepin-5-one, 4.8 g (40 mmole) of isobutyramidine hydrochloride, 10 ml (41 mmole) of a 4.12 M methanol solution of sodium methoxide and 100 ml of methanol was stirred at room temperature for 2 hr. The mixture was diluted with water and extracted with methylene chloride. The methylene chloride solution was dried over anhydrous sodium sulfate and concentrated at reduced pressure to give a yellow oil. Crystallization of the oil with ether gave a light yellow solid, mp 127°-129° C. Recrystallization from a mixture of ether and petroleum ether gave colorless rods, mp 127°-129° C.

EXAMPLE 19

2-amino-9-chloro-7-(2-chlorophenyl)-5H-pyrimido[5,4-d][2]-benzazepine

In two equal portions 14.4 g (80 mmole) of guanidine carbonate and 20 ml (82 mmole) of 4.12 M methanol solution of sodium methoxide was added over 90 min to a solution of 3.6 g (10 mmole) of 8-chloro-1-(2-chlorophenyl)-3,4-dihydro-4-[(dimethylamino)methylene]-5H-2-benzazepine-5-one in 100 ml of methanol. The mixture was diluted with water and extracted with methylene chloride. The methylene chloride solution was dried over anhydrous sodium sulfate and concentrated at reduced pressure to give a yellow oil. Crystallization of the oil with methylene chloride gave a white solid, mp 240°–241° C. Recrystallization from a mixture of ether and methylene chloride gave colorless needles, mp 240°–241° C.

EXAMPLE 20

7-(2-chlorophenyl)-2-methyl-5H-pyrimido[5,4-d][2]benzazepine methanesulfonate

In four equal portions 7.2 g (76 mmole) of acetamidine hydrochloride and 18 ml (80 mmole) of a 4.46 M methanol solution of sodium methoxide was added over a 3 hr period to a solution of 4.5 g (14 mmole) of 1-(2-chlorophenyl)-3,4-dihydro-4-[(dimethylamino)methylene]-5H-2-benzazepin-5-one in 180 ml of methanol and 180 of methylene chloride. The mixture was diluted with water, and extracted with methylene chloride. The methylene chloride solution was washed with water, dried with anhydrous sodium sulfate, and concentrated at reduced pressure to give an amber oil. The amber oil was dissolved in a mixture of 15 ml of isopropanol and 1.3 g (14 mmole) of methanesulfonic acid, and the isopropanol was removed at reduced pressure. The residue was crystallized from a mixture of ether and methylene chloride to give a light yellow solid, mp 147°–151° C. Recrystallization from a mixture of ether and methylene chloride gave yellow prisms as the half hydrate, mp 159°–160° C.

EXAMPLE 21

2-methyl-7-phenyl-5H-pyrimido[5,4-d][2]benzazepine dihydrochloride

In five equal portions 9.0 g (95 mmole) of acetamidine hydrochloride and 22.5 ml (0.1 mole) of a 4.46 M methanol solution of sodium methoxide was added over 3 hr to a solution of 4.5 g (15 mmole) of 1-phenyl-3,4-dihydro-4-[(dimethylamino)methylene]-5H-2-benzazepin-5-one in 180 ml of methanol and 180 ml of methylene chloride. The methylene chloride solution was washed with water, dried over anhydrous sodium sulfate, and concentrated at reduced pressure to give an oil. The oil was dissolved in an excess of 6% methanolic hydrogen chloride and the solvent was removed at reduced pressure to dryness. The residue was crystallized from a mixture of ether and methylene chloride to give a white solid mp 211°–221° C. Recrystallization from a mixture of methanol and ether gave white flakes, mp 217°–227° C.

EXAMPLE 22

9-chloro-7-(2-chlorophenyl)-2-methyl-5H-pyrimido[5,4-d][2]benzazepine-6-oxide

A solution of 2.0 g (5.6 mmole) of 9-chloro-7-(2-chlorophenyl)-2-methyl-5H-pyrimido[5,4-d][2]benzazepine and 2.2 g (10.8 mmole) of 85% meta-chloroperbenzoic acid in 100 ml of methylene chloride was stirred at room temperature for 21 hr. The methylene chloride solution was washed with cold dilute aqueous sodium hydroxide, dried over anhydrous sodium sulfate, and concentrated at reduced pressure to dryness. Purification by plug filtration (silica gel, 25 g; eluent 1000 ml 1:1 ether methylene chloride) gave a colorless solid, mp 215°–216° C.

EXAMPLE 23

9-chloro-7-(2-chlorophenyl)-2-methyl-5H-pyrimido[5,4-d][2]benzazepine-3,6-dioxide A solution of 3.8 g (10.7 mmole) of 9-chloro-7-(2-chlorophenyl)-2-methyl-5H-pyrimido[5,4-d][2]benzazepine and 9.6 g (47 mmole) of 85% metachloroperbenzoic acid in 400 ml of methylene chloride was stirred at room temperature for 55 hr. The methylene chloride solution was washed with cold dilute aqueous sodium hydroxide, dried over anhydrous sodium sulfate, and concentrated at reduced pressure to dryness. Purification by plug filtration (silica gel, 25 g; eluents 400 ml 1:1 ether, methylene chloride followed by 200 ml 9:1 methylene chloride, methanol) gave colorless solid, mp 241°–243° C.

EXAMPLE 24

9-chloro-7-(2-chlorophenyl)-6,7-dihydro-2-methyl-5H-pyrimido[5,4-d][2]benzazepine dihydrochloride A mixture of 3.7 g (10.5 mmole) of 9-chloro-7-(2-chlorophenyl)-2-methyl-5H-pyrimido[5,4-d][2]benzazepine, 1.3 g of zinc dust, and 40 ml of acetic acid in 90 ml of methylene chloride was stirred at −15° C. to −20° C. for 30 min. The mixture was filtered over hyflo, and the filtrate was basified with cold dilute aqueous sodium hydroxide and extracted with methylene chloride. The methylene chloride solution was dried over anhydrous sodium sulfate and concentrated at reduced pressure to give a yellow oil. The yellow oil was crystallized from an excess of 6% methanolic hydrogen chloride to give the title compound as a white solid, m.p. 272°–274° C. Recrystallization from methanol gave colorless rods, m.p. 272°–274° C.

A sample of the above material was partitioned between dilute aqueous sodium hydroxide and methylene chloride. The methylene chloride solution was dried over anhydrous sodium sulfate and concentrated at reduced pressure to dryness. The residue crystallized from ether to give the free base as cream coloed prisms, m.p. 176°–177° C.

If the reaction is carried out in acetic acid using hydrogen over a prehydrogenated platinum oxide catalyst two equivalents of hydrogen are consumed to yield on work up the tetrahydro compound described in example 40. These tetrahydro derivatives also exhibit useful CNS properties.

EXAMPLE 25

8-chloro-1-(2-chlorophenyl)-3,4-dihydro-4-[(dimethylamino)methylene]-5H-2-benzazepin-5-one A mixture of 18.6 g (61 mmole) of 8-chloro-3,4-dihydro-1-(2-chlorophenyl)-5H-2-benzazepin-5-one and 149 ml of dimethylformamide dimethyl acetal was gently heated (ca 50°) for 12 hr. The mixture was concentrated at reduced pressure to dryness. The residue was crystallized from a mixture of ether and methylene chloride to give the end product as a yellow solid, mp 170°–171° C. Recrystallization from the ether gave yellow prisms, mp 170°–171° C.

EXAMPLE 26

1-(2-chlorophenyl)-3,4-dihydro-4-[(dimethylamino)methylene]-5H-2-benzazepin-5-one A mixture of 3.4 g (12.5 mmole) of 1-(2-chlorophenyl)-3,4-dihydro-5H-2-benzazepin-5-one and 28 ml of dimethylformamide dimetyl acetal was refluxed for 2 hr. The mixture was concentrated at reduced pressure and the resulting solid was triturated with ether to give a tan solid, mp 155°–157° C. Recrystallization from a mixture of methylene chloride and ether gave yellow prisms, mp 158°–159° C.

EXAMPLE 27

3,4-Dihydro-1-phenyl-4-](dimethylamino)methylene]5H-2-benzazepin-5-one

A mixture of 5.2 g (22 mmole) of 3,4-dihydro-1-phenyl-5H-2-benzazepin-5-one and 43 ml of dimethylformamide dimethyl acetal was refluxed for 4 hr. The mixture was concentrated at reduced pressure to dryness. The residue was crystallized with ether to give a yellow solid, mp 131°–133° C. Recrystallization from ether gave yellow prisms, mp 131°–132° C.

EXAMPLE 28

9-chloro-7-(2-chlorophenyl)-2-(methylthio)-5H-pyrimido[5,4-d][2]benzazepine

A mixture of 1.1 g (3.0 mmole) of 9-chloro-7-(2-chlorophenyl)-5H-pyrimido[5,4-d][2]benzazepin-2-thiol, 1.0 ml (10 mmole) of dimethyl sulfate, 20 ml of 1N sodium hydroxide and 10 ml of ethanol was stirred at room temperature for 15 min. The mixture was diluted with water and extracted with methylene chloride. The methylene chloride solution was dried over anhydrous sodium sulfate and concentrated at reduced pressure to give an oil. Crystallization from ether gave colorless prisms, mp 187°–188° C.

EXAMPLE 29

9-chloro-7-(2-chlorophenyl)-2-(methylthio)-5H-pyrimido[5,4-d][2]benzazepine methanesulfonate The methanesulfonate salt of 9-chloro-7-(2-chlorophenyl)-2-(methylthio)-5H-pyrimido[5,4-d][2]benzazepine was prepared by the addition of equimolar amounts of the above compound and methanesulfonic acid to methanol and by precipitating the resulting salt by the addition of ether. Recrystallization from ethanol gave cream colored needles, mp 165°–166° C.

EXAMPLE 30

9-chloro-7-(2-chlorophenyl)-5H-pyrimido[5,4-d][2]benzazepine-2-thiol

A mixture of 2.8 g (7.8 mmole) of 8-chloro-1-(2-chlorophenyl)-3,4-dihydro-4-[(dimethylamino)methylene-5H-2-benzazepin-5-one, 2.8 g (37 mmole) of thiourea, and 8.0 ml (32 mmole) of a 4.0 M methanol solution of sodium methoxide in 80 ml of methanol was stirred at room temperature for 18 hr. The mixture was diluted with water and extracted with ether. The aqueous layer was neutralized with acetic acid and extracted with methylene chloride. The methylene chloride solution was dried over anhydrous sodium sulfate and concentrated at reduced pressure to give a yellow solid, mp 238°–239° C. Recrystallization from tetrahydrofuran gave yellow crystals, mp 232°–234° C.

EXAMPLE 31

Preparation of 9-chloro-7-(2-fluorophenyl)-5H-pyrimido[5,4-d][2]benzazepin-2-ol

A solution of 1.2 g (0.00354 mol) of 9-chloro-7-(2-fluorophenyl)-2-amino-5H-pyrimido[5,4-d][2]benzazepine in 20 ml of concentration sulfuric acid and 20 ml of water was refluxed for 12 hr, and then cooled. After the addition of ice, the reaction mixture was basified with ammonium hydroxide and extracted with 100 ml of dichloromethane. The solids were collected by filtration and recrystallized from dichloromethane/methanol to give the end product as white prisms, mp 297°–299° dec. The dichloromethane extract was dried, evaporated and the residue crystallized from dichloromethane/methanol to give additional product.

EXAMPLE 32

Preparation of 2,9-dichloro-7-(2-fluorophenyl)-5H-pyrimido[5,4-d][2]benzazepine

A solution of 1.0 g (0.00294 mol) of 9-chloro-7-(2-fluorophenyl)-5H-pyrimido[5,4-d][2]benzazepin-2-ol in 5 ml of phosphorous oxychloride was heated on the steam bath for 4 hr, and evaporated to dryness. The solid was crystallized from dichloromethane/ether, and the precipitate was partitioned between 50 ml of dichloromethane and 40 ml of saturated solution of sodium bicarbonate. The organic layer was dried, evaporated and crystallized from ether. Recrystallization from dichloromethane/ether gave the end product as off-white prisms, mp 157°–160°.

EXAMPLE 33

Preparation of 9-chloro-N-methyl-7-(2-fluorophenyl)-5H-pyrimido[5,4-d][2]benzazepine-2-amine A solution of 1 g(0.00279 mol) of 2,9-dichloro-7-(2-fluorophenyl)-5H-pyrimido[5,4-d][2]benzazepine in 4 ml of N,N-dimethylformamide was cooled in an ice bath and saturated with methylamine. After 64 hr at room temperature, 50 ml of ice water was added and the reaction was filtered. The precipitated was partitioned between 50 ml ofdichloromethane and 50 ml of water, and the organic layer was washed with 25 ml of brine solution, dried and evaporated to dryness. The oil was crystallized from ether and then recrystallized from dichloromethane/ether and then from methanol to give the end product as white prisms, mp 172°–179°.

EXAMPLE 34

Preparation of 9-chloro-N,N-dimethyl-7-(2-fluorophenyl)-5H-pyrimido[5,4-d][2]benzazepin-2-amine A solution of 4.0 g (0.0112 mol) of 2,9-dichloro-7-(2-fluorophenyl)-5H-pyrimido[5,4-d][2]benzazepine in 15 ml of N,N-dimethylformamide was cooled in an ice bath and saturated with dimethylamine. After 18 hr at room temperature, 80 ml of ice water was added and the precipitate was collected by filtration and recrystallized twice from methanol to give the end product as white rods, mp 175°–179°.

EXAMPLE 35

Preparation of
9-chloro-7-(2-fluorophenyl)-N-(3-N,N-dimethylaminopropyl)-5H-pyrimido[5,4-d][2]benzazepin-2-amine To 3.5 g (0.00978 mol) of 2,9-dichloro-7-(2-fluorophenyl)-5H-pyrimido[5,4-d][2]benzazepine in 7 ml of N,N-dimethylformamide was added 2.7 ml (0.0215 mol) of 3-dimethylaminopropylamine while cooling the reaction in an ice bath. After 66 hr at room temperature 50 ml of ice water was added and the reaction was filtered. The precipitate was dissolved in 50 ml of dichloromethane, washed with 40 ml of water, and evaporated. The oil was dissolved in dilute hydrochloric acid and brought to pH 2 with ammonium hydroxide. The acidic solution was extracted with dichloromethane (2×50 ml), and the acid layer was then made basic with ammonium hydroxide and extracted with 75 ml of dichloromethane which was dried and evaporated. The residue was crystallized and recrystallized from ether/petrol to give white needles, mp 90°–101°.

EXAMPLE 36

Preparation of
9-chloro-2-methoxy-7-(2-fluorophenyl)-5H-pyrimido[5,4-d][2]benzazepine To 25 ml of methanol was added 1.0 g (0.00279 mol) of 2,9-dichloro-7-(2-fluorophenyl)-5H-pyrimido[5,4d][2]benzazepine and 0.18 g (0.00335 mol) of sodium methoxide. The reaction was stirred for 18 hr, and evaporated to dryness. The solid was dissolved in 50 ml of dichloromethane and washed with 40 ml of water, dried and evaporated to dryness. The oil was crystallized and recrystallized from ether/petrol and then from ether to give the end product as white prisms, mp 137°–141°.

EXAMPLE 37

| TABLET FORMULATION (Wet granulation) | | | | | |
|---|---|---|---|---|---|
| Item | Ingredients | mg/tablet | mg/tablet | mg/tablet | mg/tablet |
| 1. | 2-amino-9-chloro-7-(2-fluorophenyl)-5H—pyrimido[5,4-d] [2] benzazepine or 7-phenyl-5H—pyrimido [5,4-d] benzazepin-2-amine | 1 | 5 | 10 | 25 |
| 2. | Lactose | 202 | 232 | 261 | 280 |
| 3. | Modified Starch | 25 | 35 | 45 | 55 |
| 4. | Pregelatinized Starch | 20 | 25 | 30 | 35 |
| 5. | Distilled Water q.s. | — | — | — | — |
| 6. | Magnesium Stearate | 2 | 3 | 4 | 5 |
| | Weight of tablet | 250 mg | 300 mg | 350 mg | 400 mg |

Procedure:
1. Mix Items 1–4 in a suitable mixer.
2. Granulate with sufficient distilled water to proper consistency. Mill.
3. Dry in a suitable oven.
4. Mill and mix with magnesium stearate for 3 minutes.
5. Compress on a suitable press equipped with appropriate punches.

EXAMPLE 38

| TABLET FORMULATION (Direct compression) | | | | | |
|---|---|---|---|---|---|
| Item | Ingredients | mg/tablet | mg/tablet | mg/tablet | mg/tablet |
| 1. | 2-amino-9-chloro-7-(2-fluorophenyl)-5H—pyrimido[5,4-d] [2] benzazepine or 7-phenyl-5H—pyrimido [5,4-d] benzazepine-2-amine | 1 | 5 | 10 | 25 |
| 2. | Lactose | 221 | 217 | 212 | 181 |
| 3. | Avicel | 45 | 45 | 45 | 55 |
| 4. | Direct Compression Starch | 30 | 30 | 30 | 35 |
| 5. | Magnesium Stearate | 3 | 3 | 3 | 4 |
| | Weight of tablet | 300 mg | 300 mg | 300 mg | 300 mg |

Procedure:
1. Mix Item 1 with an equal amount of lactose. Mix well.
2. Mix with Items 3, and 4, and the remaining amount of Item 2. Mix well.
3. Add magnesium stearate and mix for 3 minutes.
4. Compress on a suitable press equipped with appropriate punches.

EXAMPLE 39

CAPSULE FORMULATION

| Item | Ingredients | mg/tablet | mg/tablet | mg/tablet | mg/tablet |
|---|---|---|---|---|---|
| 1. | 2-amino-9-chloro-7-(2-fluorophenyl)-5H—pyrimido[5,4-d] [2] benzazepine or 7-phenyl-5H—pyrimido [5,4-d] benzazepine-2-amine | 1 | 5 | 10 | 25 |
| 2. | Lactose | 203 | 293.5 | 328 | 372.5 |
| 3. | Starch | 30 | 35 | 40 | 30 |
| 4. | Talc | 15 | 15 | 20 | 20 |
| 5. | Aerosol OT | 1 | 1.5 | 2 | 2.5 |
|   | Capsule fill weight | 250 mg | 350 mg | 400 mg | 450 mg |

Procedure:
1. Mill Items 1, 2, 3, and 5 in a suitable mixer. Mill.
2. Add talc and mix well.
3. Encapsulate on suitable equipment.

EXAMPLE 40

9-Chloro-7-(2-fluorophenyl)-5H-pyrimido[5,4d][2]benzazepine

A mixture of 34.2 g (0.1 mole) of 8-chloro-3,4-dihydro-1-(2-fluorophenyl)-4-[(dimethylamino)methylene]-5H-2-benzazepin-5-one, 62.4 g (0.6 mole) of formamidine acetate, and 35 g (0.63 mole) of sodium methoxide in 700 ml of methanol was stirred at room temperature for 3 hr, while bubbling nitrogen through the solution. The mixture was diluted with water and extracted with methylene chloride. The methylene chloride solution was dried over anhydrous sodium sulfate and concentrated at reduced pressure to give a red oil. The oil was suspended in boiling hexane and the hexane solution decanted. Upon cooling the end product was collected by filtration. Recrystallization from cyclohexane gave off-white crystals, mp 123°-125° C.

EXAMPLE 41

9-Chloro-7-(2-fluorophenyl)-5H-pyrimido[5,4-d][2]-benzazepine-6-oxide

A solution of 3.2 g (10 mmoles) of 9-chloro-7-(2-fluorophenyl)-5H-pyrimido[5,4-d][2]benzazepine, 3 g (15 mmoles) of 85% m-chloroperbenzoic acid in 100 ml of methylene chloride was stirred at room temperature for 4 hours. The reaction mixture was washed with an excess of ice cold dilute sodium hydroxide, dried over anhydrous sodium sulfate and filtered over hyflo. The filrate was concentrated at reduced pressure to dryness. The residue was crystallized from a mixture of methylene chlorine and ether to give the crude product, m.p. 185°-186° C. Recrystallization from a mixture of methylene chloride and ether gave the pure product, m.p. 187°-188° C.

EXAMPLE 42

9-Chloro-7-(2-fluorophenyl)-5H-pyrimido[5,4-d][2]benzazepin-5-ol acetate

A mixture of 2.5 g (7.4 mmols) of 9-chloro-7-(2-fluorophenyl)-5H-pyrimido[5,4-d][2]benzazepine-6-oxide and 50 ml of acetic anhydride was heated on the steambath for 24 hours. The reaction mixture was concentrated at reduced pressure to dryness and the residue was crystallized from a mixture of methylene chloride and ether to give the crude product, m.p. 197°-198° C. Recrystallization from a mixture of methylene chloride and ether gave the pure product as cream colored prisms, m.p. 200°-201° C.

EXAMPLE 43

9-Chloro-7-(2-chlorophenyl)-4,5,6,7-tetrahydro-2-methyl-1H-pyrimido[5,4d][2]benzazepine, hydrochloride salt A solution of 3.8 g (10.7 mmole) of 9-chloro-7-(2-chlorophenyl)-2-methyl-5H-pyrimido[5,4-d][2]benzazepine in 50 ml of acetic acid was hydrogenated at room temperature and atmospheric pressure in the presence of 0.5 g of prehydrogenated platinum oxide. After 3 hours about 500 ml (ca 2 equivalent) of hydrogen was absorbed and the catalyst was separated by filtration. The filtrate was concentrated at reduced pressure to dryness. The residue was dissolved in methylene chloride, washed with an excess of dilute ice cold sodium hydroxide, and dried over anhydrous sodium sulfate. The methylene chloride solution was diluted with an excess of methanolic hydrogen chloride and concentrated at reduced pressure. The residue was triturated with isopropanol and the crude product was collected by filtration. Recrystallization from methanol gave the pure product, m.p. 275°-276° C.

EXAMPLE 44

2-Amino-9-chloro-7-(2-fluorophenyl)-5H-pyrimido[5,4-d][2]benzazepine-6-oxide In two equal portions 28 g (150 mmole) of guanidine carbonate and 38 ml (150 mmole) of a 4.09 M methanol solution of sodium methoxide was added over a 2 hr period to a solution of 7.0 g (20 mmole) of 8-chloro-1-(2-fluorophenyl)-3,4-dihydro-4-[(dimethylamino)methylene]-5H-2-benzazepin-5-one-2-oxide in 210 ml of methanol. The mixture was diluted with water and extracted with methylene chloride. The methylene chloride solution was dried over anhydrous sodium sulfate and concentrated at reduced pressure to give a red solid. Recrystallization from a mixture of methanol and ethyl acetate gave the product as fine yellow needles, m.p. 320°-323° C.

EXAMPLE 45

9-Chloro-7-(2-chlorophenyl)-6,7-dihydro-2,6-dimethyl-5H-pyrimido[5,4-d][2]benzazepine A mixture of 4 g (11 mmole) of 9-chloro-7-(2-chlorophenyl)-6,7-dihydro-2-methyl-5H-pyrimido[5,4d][2-

]benzazepine 2 ml of 88% formic acid and 2 ml of 37.5% formaldehyde solution was heated on the steambath for 3 hours. The reaction mixture was poured into an excess of dilute ice cold sodium hydroxide and extracted with methylene chloride. The methylene chloride solution was dried over anhydrous sodium sulfate and concentrated at reduced pressure to dryness. The residue was crystallized from ether to give the crude product, m.p. 155°–156° C. Recrystallization from ether gave the pure product as colorless prisms, m.p. 156°–157° C.

EXAMPLE 46

8-Chloro-1-(2-fluorophenyl)-3,4-dihydro-4-[(dimethylamino)methylene]-5H-2-benzazepin-5-one

Method A

A mixture of 7.2 g (25 mmole) of 8-chloro-1-(2-fluorophenyl)-3,4-dihydro-5H-2-benzazepin-5-one and 50 ml of dimethylformamide dimethyl acetal was refluxed for 1 hr. The mixture was concentrated at reduced pressure to give tan crystals. Recrystallization from ether gave yellow prisms, m.p. 228°–233° C.

Method B

A mixture of 10 g (35 mmole) of crude 8-chloro-3,4-dihydro-1-(2-fluorophenyl)-5H-2-benzazepin-5-one and 10 g (84 mmole) of dimethylformamide dimethyl acetal in 10 ml of dimethylformamide was stirred at room temperature for 12 hr. The resulting precipitate was collected by filtration, and washed successively with ethanol and ether to give tan crystals which were identical in every respect to an authentic sample.

EXAMPLE 47

8-Chloro-1-phenyl-3,4-dihydro-4-[(dimethylamino)methylene]-5H-2-benzazepin-5one

The preparation of 8-chloro-1-phenyl-3,4-dihydro-4-[(dimethylamino)methylene]-5H-2-benzazepin-5-one was conducted in the same manner as the preparation of 8-chloro-1-(2-fluorophenyl)-3,4-dihydro-4-[(dimethylamino)methylene]-5H-2-benzazepin-5-one (Method A) to give yellow prisms, m.p. 180°–183° C.

EXAMPLE 48

8-Chloro-1-(2-fluorophenyl)-3,4-dihydro-5H-2-benzazepin-5-one-2-oxide

A mixture of 6.4 g (22 mmol) of 8-chloro-1-(2-fluorophenyl)-3,4-dihydro-5H-2-benzazepin-5-one and 6.4 g (34 mmole) of m-chloroperbenzoic acid in 350 ml of methylene chloride was stirred at room temperature for 2 hr. The methylene chloride solution was washed with saturated aqueous sodium bicarbonate and water, dried over anhydrous sodium sulfate and concentrated at reduced pressure to give a yellow oil. The oil was crystallized from a mixture of ether and petroleum ether to give off-white prisms, mp 166°–168° C. Recrystallization from a mixture of ether and methylene chloride gave colorless prisms, mp 168°–170° C.

EXAMPLE 49

8-Chloro-1-(2-chlorophenyl)-3,4-dihydro-5H-2-benzazepin-5-one-2-oxide

The preparation of 8-chloro-1-(2-chlorophenyl)-3,4-dihydro-5H-2-benzazepin-5-one-2-oxide was conducted in the same manner as the preparation of 8-chloro-1-(2-fluorophenyl)-3,4-dihydro-5H-2-benzazepin-5-one-2-oxide to give yellow prisms, mp 184°–187° C.

EXAMPLE 50

8-Chloro-1-(2-fluorophenyl)-3,4-dihydro-4-[(dimethylamino)methylene]-5H-2-benzazepin-5-one-2-oxide A mixture of 3.4 g (11 mmole) of 8-chloro-1-(2-fluorophenyl)-3,4-dihydro-5H-2-benzazepin-5-one-2-oxide and 26 ml of dimethylformamide dimethyl acetal was stirred at room temperature for 12 hr. The mixture was diluted with ether and the precipitate collected to give a yellow solid, mp 175°–178° C. Recrystallization from a mixture of ether and ethyl acetate gave yellow needles, mp 193°–194° C.

EXAMPLE 51

8-Chloro-1-(2-chlorophenyl)-3,4-dihydro-4-[(dimethylamino)methylene]-5H-2-benzazepin-5-one-2-oxide The preparation of 8-chloro-1-(2-chlorophenyl)-3,4-dihydro-4-[(dimethylamino)methylene]-5H-2-benzazepin-5-one-2-oxide was prepared in the same manner as the preparation of 8-chloro-1-(2-fluorophenyl)-3,4-dihydro-4-[(dimethylamino)methylene]-5H-2-benzazepin-5-one-2-oxide to give yellow prisms, mp 196°–198° C.

EXAMPLE 52

9-Chloro-7-(2-chlorophenyl)-2-methyl-5H-pyrimido[5,4-d][2]-benzazepine-6-oxide

A mixture of 1 g (2.8 mmole) of 8-chloro-1-(2-chlorophenyl)-4-[(dimethylamino)methylene]-3,4-dihydro-5H-2-benzazepine-5-one-2-oxide, 1.0 g (11 mmole) of acetamidine hydrochloride and 2.0 ml (9.9 mmole) of a 4.46M methanol sulution of sodium methoxide in a mixture of 20 ml of methanol and 20 ml of methylene chloride was stirred at room temperature for 2 hr. The mixture was diluted with water and extracted with methylene chloride. The methylene chloride solution was washed with water, dried over anhydrous sodium sulfate and concentrated at reduced pressure to dryness. Recrystallization of the residue from a mixture of ether and methylene chloride gave a colorless solid, mp 215°–216° C.

EXAMPLE 53

9-Chloro-7-(2-fluorophenyl)-5H-pyrimido[5,4-d][2]benzazepin-5-ol

A solution of 3.7 g (9.7 mmole) of 9-chloro-7-(2-fluorophenyl)-5H-pyrimido[5,4-d][2]benzazepin-5-ol acetate in a mixture of 25 ml of tetrahydrofuran, 50 ml of methanol and 2 ml of 3N sodium hydroxide was stirred at room temperature for 0.5 hr. The reaction mixture was poured into ice water and extracted with methylene chloride. The organic layer was separated, dried over anhydrous sodium sulfate and concentrated in vacuo to dryness. The residue crystallized from a mixture of methylene chloride and ether to give a crude product melting at 186°–188° C. Recrystallization from a mixture of ether and methylene chloride gave the product as cream colored prisms, mp 196°–198° C.

EXAMPLE 54

9-Chloro-7-(2-chlorophenyl)-5H-pyrimido[5,4-d][2]benzazepine-6-oxide

A solution of 6.8 g (20 mmole) of 9-chloro-7-(2-chlorophenyl)-5H-pyrimido[5,4-d][2]benzazepine, 6 g (30 mmole) of 85% m-chloroperbenzoic acid in 200 ml of methylene chloride was stirred at room temperature for 4 hrs. The mixture was washed with an excess of ice cold dilute sodium hydroxide, dried over anhydrous sodium sulfate and filtered over hyflo. The filtrate was concentrated at reduced pressure to dryness. The residue was crystallized from a mixture of methylene chloride and ether to give a crude product, mp 228°–229° C. Recrystallization from a mixture of methylene chloride and ether gave the product, mp 216°–217° C.

EXAMPLE 55

9-Chloro-7-(2-chlorophenyl)-5H-pyrimido[5,4-d][2]benzazepin-5-ol acetate

A mixture of 3 g (8 mmole) of 9-chloro-7-(2-chlorophenyl)-5H-pyrimido[5,4-d][2]benzazepine-6-oxide and 50 ml of acetic anhydride was heated on the steam bath for 22 hrs. The reaction mixture was concentrated at reduced pressure to dryness and the residue was crystallized from a mixture of methylene chloride and ether to give a product of mp 211°–212° C. Recrystallization from a mixture of methylene chloride and ether gave the pure product as colorless prisms, mp 211°–212° C.

EXAMPLE 56

9-Chloro-7-(2-chlorophenyl)-5H-pyrimido[5,4-d][2]benzazepin-5-ol

A solution of 4.8 g (12 mmole) of 6-chloro-7-(2-chlorophenyl)-5-pyrimido[5,4-d][2]benzazepin-5-ol acetate in a mixture of 50 ml of tetrahydrofuran, 50 ml of methanol and 4 ml of 3N sodium hydroxide was stirred at room temperature for 30 min. The reaction mixture was poured into ice water and extracted with methylene chloride. The organic layer was separated, dried over anhydrous sodium sulfate and concentrated at reduced pressure to dryness. The residue was crystallized from a mixture of methylene chloride and ether to give a product of mp 105°–117° C. Recrystallization from a mixture of methylene chloride and acetone gave the pure product as colorless prisms, mp 174°–175° C.

EXAMPLE 57

9-Chloro-7-(2-fluorophenyl)-2-(4-methyl-1-piperazinyl)-5H-pyrimido[5,4-d][2]benzazepine hydrochloride To a solution of 3.0 g (0.00838 mol) of 2,9-dichloro-7-(2-fluorophenyl)-5H-pyrimido[5,4-d][2]benzazepine in 8 ml of N,N-dimethylformamide was added 2 g (0.02 mol) of N-methylpiperazine. After 20 hr ice water (40 ml) was added to the reaction which was then filtered. The solid was partitioned between 50 ml of dichloromethane and 50 ml of 1N hydrochloric acid, and the pH was adjusted to 1–2 with ammonium hydroxide. The resulting precipitate was filtered and recrystallized twice from methanol to give white prisms, mp 187°–194° C. The acid layer was made basic with ammonium hydroxide, and extracted with 100 ml of dichloromethane which was dried and evaporated. The oil was acidified with 1N hydrochloric acid, adjusted to pH 1–2 with ammonium hydroxide, cooled and filtered. The precipitate was recrystallized from methanol to give a further crop of the product.

EXAMPLE 58

9-Chloro-2-methoxy-7-(2-fluorophenyl)-5H-pyrimido[5,4-d][2]benzazepine

To 25 ml of methanol was added 1.0 g (0.00279 mol) of 2,9-dichloro-7-(2-fluorophenyl)-5H-pyrimido[5,4-d][2]benzazepine and 0.18 g (0.00335 mol) of sodium methoxide. The reaction was stirred for 18 hr, and evaporated to dryness. The solid was dissolved in 50 ml of dichloromethane and washed with 40 ml of water, dried and evaporated to dryness. The oil was crystallized and recrystallized from ether/petrol and then from ether to give white prisms, mp 137°–141° C.

EXAMPLE 59

9-Chloro-7-(2-fluorophenyl)-5H-pyrimido[5,4-d][2]benzazepine-2-acetic acid ethyl ester To 20 ml of dimethylmalonate was added 1.9 g (16.8 mmol) of potassium tertiary butoxide with stirring under nitrogen, and after 15 min, 2.0 g (5.59 mmol) of 2,9-dichloro-7-(2-fluorophenyl)-5H-pyrimido[5,4-d][2]benzazepine was added. The reaction was kept at 110° C. for 2 hr and 140° C. for 4 hr. Ice was added to the reaction mixture which was then acidified with concentrated hydrochloric acid, and extracted with 100 ml of ether. The ether layer was extracted with 25 ml of 3N hydrochloric acid, and the combined acid layers were made basic with ammonium hydroxide and extracted with ether (2×100 ml). The solution was dried, charcoal filtered and concentrated to a small volume. Petroleum ether was added and the product was filtered and recrystallized from the same solvents to give white rods, mp 98°–103° C.

EXAMPLE 60

9-Chloro-7-(2-fluorophenyl)-5H-pyrimido[5,4-d][2]benzazepine-2-acetic acid

A solution of 4.0 g (9.76 mmol) of 9-chloro-7-(2-fluorophenyl)-5H-pyrimido[5,4-d][2]benzazepine-2-acetic acid ethyl ester in 30 ml of ethanol and 25 ml of 1N sodium hydroxide was heated on the steam bath for 3 hr. The mixture was partitioned between 75 ml of water and 75 ml of ether. The basic layer was acidified with acetic acid and extracted with dichloromethane (2×100 ml), which was dried and evaporated. The resulting oil was crystallized from methanol and recrystallized from dichloromethane/ether/petroleum ether to give off-white prisms, mp 138°–140° C.

EXAMPLE 61

9-Chloro-7-(2-fluorophenyl)-N-methyl-5H-pyrimido[5,4-d][2]benzazepine-2-acetamide Methylamine was bubbled into a solution of 2.6 g (6.34 mmol) of 9-chloro-7-(2-fluorophenyl)-5H-pyrimido[5,4-d][2]benzazepine-2-acetic acid ethylester in 60 ml of ethanol for 10 min. After standing for 18 hr, the reaction was evaporated and the residue was partitioned between 75 ml of dichloromethane and 50 ml of water. The organic layer was dried and evaporated. The residue was crystallized and then recrystallized from dichloromethane/ether to give white rods, mp 175°–177° C.

EXAMPLE 62

9-Chloro-7-(2-chlorophenyl)-5H-pyrimido[5,4-d][2]benzazepine

A mixture of 90.5 g (0.25 mol) of 8-chloro-1-(2-chlorophenyl)-3,4-dihydro-4-[(dimethylamino)methylene]-5H-2-benzazepine-5-one, 100 g (0.96 mol) of formamidine acetate and 1.0 L of formamide was heated on a steam bath for 16 hr. The mixture was cooled to 0° and the resulting precipitate collected by filtration. The precipitate was washed with water and dried to constant weight to give off-white crystals, mp 120°–121° C.

EXAMPLE 63

9-Chloro-7-(2-fluorophenyl)-5H-pyrimido[5,4-d][2]benzazepine-6-oxide

A mixture of 0.4 g (1.1 mmol) of 8-chloro-1-(2-fluorophenyl)-3,4-dihydro-4-[(dimethylamino)methylene]-5H-2-benzazepin-5-one 2-oxide, 1.0 g (9.6 mmol) of formamidine acetate and 20 ml of formamide was heated on a steam bath for 6 hr. The mixture was poured over ice and extracted with methylene chloride. The methylene chloride solution was washed with water, dried over anhydrous sodium sulfate and concentrated at reduced pressure. The residue crystallized with the addition of a mixture of ether and methylene chloride to give off-white crystals, mp 186°–188° C.

EXAMPLE 64

9-Chloro-7-(2-chlorophenyl)-5H-pyrimido[5,4-d][2]benzazepine-6-oxide

A mixture of 0.4 g (1.1 mmol) of 8-chloro-1-(2-chlorophenyl)-3,4-dihydro-4-[(dimethylamino)methylene]-5H-2-benzazepin-5-one 2-oxide and 1.0 g (9.6 mmol) of formamidine acetate in 20 ml of formamide was heated on a steam bath for 7 hr. The mixture was poured over ice and extracted with methylene chloride. The methylene chloride solution was washed with water, dried over anhydrous sodium sulfate and concentrated at reduced pressure. The residue was triturated with ether to give an off-white solid, mp 215°–217° C.

EXAMPLE 65

9-Chloro-7-(2-chlorophenyl)-5H-pyrimido[5,4-d][2]benzazepine

A mixture of 0.5 g (1.3 mmol) of 9-chloro-7-(2-chlorophenyl)-5H-pyrimido[5,4-d][2]benzazepine-6-oxide and 1.0 ml (10 mmol) of phosphorous trichloride in 20 ml of methylene chloride was refluxed for 3 hr. The mixture was cooled, poured over ice, basified with ammonium hydroxide and extracted with methylene chloride. The methylene chloride solution was washed with water, dried over anhydrous sodium sulfate and concentrated at reduced pressure. The residue crystallized upon the addition of ether to give colorless prisms, mp 121°–123° C.

EXAMPLE 66

9-Chloro-7-(2-fluorophenyl)-5H-pyrimido[5,4-d][2]benzazepine

A mixture of 0.5 g (1.5 mmol) of 9-chloro-7-(2-fluorophenyl)-5H-pyrimido[5,4-d][2]benzazepine-6-oxide, and 1.0 mol (10 mmol) of phosphorous trichloride in 20 ml of methylene chloride was heated at reflux for 2 hr. The mixture was poured over ice, basified with ammonium hydroxide and extracted with methylene chloride. The methylene chloride solution was dried over anhydrous sodium sulfate and concentrated at reduced pressure to dryness. The residue was crystallized from ether to give off-white crystals, mp 122°–124° C.

EXAMPLE 67

9-Chloro-7-(2-fluorophenyl)-5H-pyrimido[5,4-d][2]benzazepine-2-thiol-6-oxide

A mixture of 1.5 g (4 mmol) of 8-chloro-1-(2-fluorophenyl)-3,4-dihydro-4-[(dimethylamino)methylene]-5H-2-benzazepin-5-one-2-oxide, 1.5 g (20 mmol) of thiourea and 5 ml of a 4M methanol solution of sodium methoxide in 30 ml of methanol was stirred at room temperature for 5 hr. The mixture was poured into water and extracted with ether. The aqueous solution was acidified with acetic acid and extracted with methylene chloride. The methylene chloride solution was dried over anhydrous sodium sulfate and concentrated at reduced pressure. The residue was triturated with methylene chloride to give an orange solid. Recrystallization from methylene chloride gave the product as orange crystals, mp 323°–325° C. (dec.).

EXAMPLE 68

9-Chloro-7-(2-chlorophenyl)-6,7-dihydro-5H-pyrimido[5,4-d][2]benzazepine

A mixture of 68 g (0.2 mol) of 9-chloro-7-(2-chlorophenyl)-5H-pyrimido[5,4-d][2]benzazepine, 27 g of zinc dust and 250 ml of acetic acid in 600 ml of methylene chloride was stirred at −30° C. for 2 hr. The mixture was filtered over hyflo into a stirred mixture of 600 ml of concentrated ammonium hydroxide and 500 ml of ice. The methylene chloride solution was separated, dried over anhydrous sodium sulfate and concentrated at reduced pressure. The residue crystallized from a mixture of methylene chloride and ether to give the product as a colorless solid. Recrystallization from a mixture of ether and methylene chloride gave the product as colorless needles, mp 169°–170° C.

EXAMPLE 69

9-Chloro-7-(2-chlorophenyl)-6,7-dihydro-6-[(4-methylphenyl)sulfonyl]-5H-pyrimido[5,4-d][2]benzazepine A solution of 14.5 g (42 mmole) of 9-chloro-7-(2-chlorophenyl)-6,7-dihydro-5H-pyrmido[5,4-d][2]benzazepine, 14.5 g (76 mmols) of p-toluene-sulfonyl chloride, 30 ml of pyridine and 0.3 g of 4-dimethylaminopyridine in 300 ml of methylene chloride was stirred at room temperature for 24 hr. The mixture was washed with an excess of dilute ice cold hydrochloric acid and dilute aqueous sodium hydroxide. The methylene chloride solution was dried over anhyrous sodium sulfate and concentrated at reduced pressure to dryness. The residue crystallized from a mixture of methylene chloride and ether to give the product as a white solid, mp 200°–201° C. Recrystallization from a mixture of ether and methylene chloride gave the pure product as colorless prisms, mp 200°–201° C.

EXAMPLE 70

9-Chloro-7-(2-chlorophenyl)-6,7-dihydro-6-(trifluoroacetyl)-5H-pyrimido[5,4-d][2]benzazepine Dropwise 5.0 ml (35 mmol) of trifluoroacetic anhydride was added to a solution of 6.4 g (19 mmol) of 9-chloro-7-(2-chlorophenyl)-6,7-dihydro-5H-pyrimido[5,4-d][2]benzazepine and 10 ml (12.8 mmol) of pyridine in 75 ml of methylene chloride which was cooled to 0° C. After stirring for 1 hr, the mixture was poured into ice cold dilute hydrochloric acid. The methylene chloride solution was separated, washed with saturated aqueous sodium chloride, dried over anhydrous sodium sulfate and concentrated at reduced pressure. The residue was crystallized from ether to give the product as pink crystals, mp 178°–179° C. Recrystallization from ether gave the product as off-white crystals, mp 179°–180° C.

EXAMPLE 71

9-Chloro-7-(2-chlorophenyl)-6,7-dihydro-6-[(4-methylphenyl)sulfonyl]-5H-pyrimido[5,4-d][2]benzazepine-3-oxide A solution of 7.6 g (15 mmol) of 9-chloro-7-(2-chlorophenyl)-6,7-dihydro-6-[(4-methylphenyl)sulfonyl]-5H-pyrimido[5,4-d][2]benzazepine and 4.0 g (20 mmol) of mchloroperbenzoic acid in 300 ml of methylene chloride was stirred at room temperature for 48 hr. The mixture was washed with cold dilute sodium hydroxide and saturated aqueous sodium chloride. The methylene chloride solution was dried over anhydrous sodium sulfate and concentrated at reduced pressure to dryness. The residue (8.2 g) was purified by column chromatography (silica gel, 20 g; eluents, methylene chloride then ethyl acetate) the methylene chloride eluent gave 2.0 g of the starting material as a colorless solid. The ethyl acetate eluent gave 2.1 g of the product as an off-white solid, mp, 242°–243° C. Recrystallization from a mixture of ether and methylene chloride gave the product as colorless crystals, mp 243°–244° C.

EXAMPLE 72

9-Chloro-7-(2-chlorophenyl)-5H-pyrimido[5,4-d][2]benzazepine-3-oxide

Method A

A mixture of 2.0 g (3.9 mmol) of 9-chloro-7-(2-chlorophenyl)-6,7-dihydro-6-[(4-methylphenyl)sulfonyl]-5H-pyrimido[5,4-d][2]benzazepine-3-oxide and 8 ml of a 4M methanol solution of sodium methoxide in a mixture of 130 ml of tetrahydrofuran and 180 ml of methanol was stirred at room temperature for 19 hr. The mixture was poured into an ice cold sodium chloride solution and extracted with methylene chloride. The methylene chloride solution was washed with aqueous sodium chloride, dried over anhydrous sodium sulfate and concentrated at reduced pressure. The residue was purified by column chromatography (silica gel, 20 g; eluents 20% ether in methylene chloride then 10% methanol in methylene chloride) to give the product in the 10% methanol in methylene chloride eluent as a white solid. Recrystallization from a mixture of methylene chloride and ether gave the product as long colorless prisms, mp 189°–190° C.

Method B

A mixture of 1.5 g (4.3 mmol) of 9-chloro-7-(2-chlorophenyl)-6,7-dihydro-5H-pyrimido[5,4-d][2]benzazepine-3-oxide, and 6 ml of a 5% methylene chloride solution of bromine in 600 ml of methylene chloride was stirred at room temperature for 30 min. The mixture was basified with the addition of 4.5 ml (32 mmol) of triethylamine and stirred for 10 min. The mixture was washed with saturated aqueous sodium chloride, dried over anhydrous sodium sulfate and concentrated at reduced pressure. The residue was purified by column chromatography (silica gel, 50 g; eluents methylene chloride then ethyl acetate then 30% tetrahydrofuran in methylene chloride). The ethyl acetate eluent contained a colorless solid, mp 242°–244° C. which was identified as a compound isomeric about the imine bond with the product. The 30% tetrahydrofuran in methyl chloride eluent contained the product as colorless prisms, mp 189°–190° C.

EXAMPLE 73

9-Chloro-7-(2-chlorophenyl)-6,7-dihydro-6-(trifluoroacetyl)-5H-pyrimido[5,4-d][2]benzazepine-3-oxide The preparation of 9-chloro-7-(2-chlorophenyl)-6,7-dihydro-6-(trifluoroacetyl)-5H-pyrimido[5,4-d][2]benzazepine-3-oxide was conducted in the same manner as the preparation of 9-chloro-7-(2-chlorophenyl-6,7-dihydro-6-[(4-methylphenyl)sulfonyl]-5H-pyrimido[5,4-d][2]benzazepine-3-oxide to give the product as colorless crystals, mp 209°–211° C.

EXAMPLE 74

9-Chloro-7-(2-chlorophenyl)-6,7-dihydro-5H-pyrimido[5,4-d][2]benzazepine-3-oxide A mixture of 4.9 g (11 mmol) of 9-chloro-7-(2-chlorophenyl)-6,7-dihydro-6-trifluoroacetyl)-5H-pyrimido[5,4-d][2]benzazepine-3oxide, 50 ml of 3N aqueous sodium hydroxide, 100 ml of ethanol and 100 ml of tetrahydrofuran was stirred at room temperature for 30 min. The mixture was concentrated at reduced pressure to a small volume. The resulting precipitate was collected by filtration to give a colorless solid, mp 259°–260° C. Recrystallization from tetrahydrofuran gave the product as colorless crystals, mp 263°–264° C.

What is claimed:

1. A compound of the formula

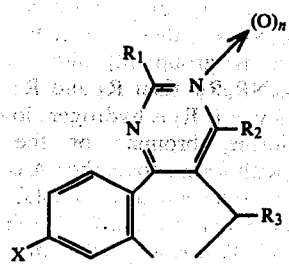

wherein A is selected from the group consisting of

\
C=N
/

\
C=N
/→O

\
CH—NH
/

Y         Y         Y and (a)        (b)        (c)

\
CH—N
/
  \
   lower alkyl;
  Y (d)

$R^1$ is selected from the group consisting of hydrogen, chlorine, bromine, lower alkyl, the group $NR_4R_5$, the group —$CH_2$—CO—$R_7$, the group —$NH(CH_2)_mNR_8R_9$, hydroxy, lower alkoxy, mercapto and lower alkyl mercapto; $R_2$ is hydrogen; $R_3$ is selected from the group consisting of hydrogen, the radical of the formula

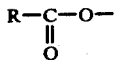

wherein R is lower alkyl or hydrogen and hydroxy; X is selected from the group consisting of hydrogen, halogen, trifluoromethyl, ethyl, α-hydroxy ethyl and acetyl; Y is hydrogen or halogen; $R_4$ and $R_5$ are hydrogen or lower alkyl or together with their co-bonded nitrogen atom form a five to seven membered heterocyclic group selected from the group consisting of morpholino, piperidino, 3-pyrrolino, piperazino, azetidino, aziridino, pyrrolidino and hexamethyleneimino; $R_7$ is selected from the group consisting of hydroxy, lower alkoxy and $NR_8R_9$; $R_8$ and $R_9$ are hydrogen or lower alkyl; n is 0 or 1 and m is 1 to 7 with the limitation that (1) when $R_3$ is the radical

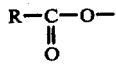

or hydroxy, A is the group (a), X is hydrogen, halogen, trifluoromethyl, ethyl or acetyl and $R_1$ is the group —$NH(CH_2)_mNR_8R_9$, then $R_8$ and $R_9$ are lower alkyl, (2) when A is group (d) and $R_1$ is the group —$NH(CH_2)_mNR_8R_9$, then $R_8$ and $R_9$ are lower alkyl and (3) when n is 1, $R_1$ is hydrogen, lower alkyl, lower alkoxy, chlorine, bromine or the group —$CH_2$—CO—$R_7$ with $R_7$ as above, then A is the group (a) or (b) and the pharmaceutically acceptable salts thereof.

2. The compound of claim 1 wherein A is group (b), $R_1$ is amino, n is 0, X is selected from the group consisting of hydrogen, halogen and trifluoromethyl and Y is hydrogen or halogen.

3. The compound of claim 1 wherein $R_1$ is selected from the group consisting of hydrogen, chlorine, bromine, lower alkyl, the group —$NH(CH_2)_mNR_8R_9$ wherein m is 1 to 7 and $R_8$, $R_9$ are hydrogen or lower alkyl, the group —$CH_2$—CO—$R_7$, hydroxy lower alkoxy, mercapto and lower alkyl mercapto; $R_7$ is lower alkoxy or dialkylaminoalkylamino; and $R_2$ is hydrogen.

4. The compound of claim 1 wherein A is group (a) and n is 0.

5. The compound of claim 4 wherein $R_2$ and $R_3$ are hydrogen; $R_1$ is selected from the group consisting of hydrogen, lower alkyl, the group $NR_4R_5$ wherein $R_4$ and $R_5$ are hydrogen or lower alkyl, hydroxy, chlorine, bromine, the group —$NH(CH_2)_mNR_8R_9$ wherein $R_8$ and $R_9$ are lower alkyl and the group —$CH_2$—CO—$R_7$.

6. The compound of claim 5 wherein $R_1$ is selected from the group consisting of hydrogen, amino and lower alkyl.

7. The compound of claim 4 wherein $R_2$ is hydrogen; $R_3$ is hydroxy and $R_1$ is selected from the group consisting of hydrogen, lower alkyl and the group $NR_4R_5$ wherein $R_4$ and $R_5$ are hydrogen or lower alkyl.

8. The compound of claim 4 wherein $R_1$ and $R_3$ are hydrogen and $R_2$ is amino or di-lower alkylmino.

9. The compound of claim 8 wherein $R_2$ is dimethylamino.

10. The compound of claim 1 wherein X is halogen.

11. The compound of claim 10 wherein X is chlorine.

12. The compound of claim 11 wherein Y is selected from the group consisting of hydrogen, chlorine and fluorine.

13. The compound: 9-chloro-7-(2chlorophenyl)-5H-pyrimido[5,4-d][2]benzazepine.

14. The compound: b 9-chloro-7-(2-fluorophenyl)-5H-pyrimido[5,4-d][2]benzazepine.

15. The compound: 9-chloro-7-(2-chlorophenyl)-2-methyl-5H-pyrimido[5,4-d][2]benzazepine.

16. The compound: 9-chloro-7-(2-fluorophenyl)-N,N-dimethyl-5H-pyrimido[5,4-d][2]benzazepine-4-amine.

17. The compound: 9-chloro-7-(2fluorophenyl)-5H-pyrimido[5,4-d][2]benzazepin-2ol.

18. The compound: 9-chloro-N,N-dimethyl-7-(2-fluorophenyl)-5H-pyrimido[5,4-d][2benzazepin-2amine.

* * * * *